United States Patent
Ryan et al.

(10) Patent No.: US 8,501,432 B2
(45) Date of Patent: Aug. 6, 2013

(54) PROCESSING OF NANOPARTICLES

(75) Inventors: Kevin M. Ryan, County Limerick (IE); Ambarish Sanyal, Limerick (IE); Timothy McGloughlin, County Limerick (IE); Anna V. Piterina, Limerick (IE)

(73) Assignee: University of Limerick, Limerick (IE)

( * ) Notice: Subject to any disclaimer, the term of this patent is extended or adjusted under 35 U.S.C. 154(b) by 315 days.

(21) Appl. No.: 12/923,722

(22) Filed: Oct. 5, 2010

(65) Prior Publication Data
US 2011/0091925 A1 Apr. 21, 2011

(30) Foreign Application Priority Data

Oct. 5, 2009 (IE) .................................. 2009/0775
Oct. 23, 2009 (IE) .................................. 2009/0822

(51) Int. Cl.
*C12Q 1/02* (2006.01)
*H01B 1/00* (2006.01)
*H01B 1/12* (2006.01)
*C09K 11/02* (2006.01)

(52) U.S. Cl.
USPC ........ 435/29; 252/301.35; 252/500; 977/773; 977/904

(58) Field of Classification Search
USPC ................ 252/500, 301.35; 435/29; 977/773, 977/904
See application file for complete search history.

(56) References Cited

U.S. PATENT DOCUMENTS
2006/0275757 A1* 12/2006 Lee et al. ........................ 435/6

OTHER PUBLICATIONS

Ambarish Sanyal, Tanushree Bala, Shafaat Ahmed, Ajay Singh, Anna V. Piterina, Timothy M. McGloughlin, Fathima R. Laffira and Kevin M. Ryan, Water dispersible semiconductor nanorod assemblies via a facile phase transfer and their application as fluorescent biomarkers, J. Mater. Chem., 2009, 19, 8974-8981.*
A. P. Alivisatos, "Perspectives on the Physical Chemistry of Semiconductor Nanocrystals," The Journal of Physical Chemistry A, 1996, vol. 100, pp. 13226-13239.
Chia-Cheng Kang et al., "2D Self-Bundled CdS Nanorods with Micrometer Dimension in the Absence of an External Directing Process," American Chemical Society Nano Letters, 2008, vol. 2, No. 4, pp. 750-756.
I. Gur et al., "Air-Stable All-Inorganic Nanocrystal Solar Cells Processed from Solution," Science, Oct. 21, 2005, vol. 310, 10 pages.
N. C. Greenham et al., "Charge Separation and transport in conjugated-polymer/semiconductor-nanocrystals composites studied by photoluminescence quenching and photoconductivity," Journal of the American Physical Society—Physical Review B, Dec. 15, 1996, vol. 54, No. 24, pp. 17628-17637.

(Continued)

*Primary Examiner* — Bijan Ahvazi
(74) *Attorney, Agent, or Firm* — Jacobson Holman PLLC

(57) ABSTRACT

Ligand-capped nanoparticles are dispersed in an organic solvent. There is then phase transfer of the nanoparticles introducing into the organic solvent an aqueous solution of polymer surfactant dissolved in water. The organic solvent and the aqueous solution are then mixed until the polymer forms micelles which encapsulate the nanoparticles in assemblies. The resultant nanoparticle assemblies in an aqueous phase may be used for any of a range of desired applications. It has been found that the assembly size can be tuned by control of any or a combination of method parameters such as concentration of polymer surfactant, and/or temperature of the phase change reaction, and/or rate of mixing, such as rotational rate of stirring. The nanoparticle assemblies find particular application as fluorescent biomarkers.

24 Claims, 13 Drawing Sheets

OTHER PUBLICATIONS

R. Xie et al., "Colloidal InP Nanocrystals as Efficient Emitters Covering Blue to Near-Infrared," Journal of the American Chemical Society, 2007, vol. 129, pp. 15432-15433.
U. Westedt et al., "Deposition of Nanoparticles in the Arterial Vessel by Porous Balloon Catheters: Localization by Confocal Laser Scanning Microscopy and Transmission Electron Microscopy," AAPS Journal, 2002, vol. 4, No. 4, article 41, http://www.aapspharmsci.org, pp. 1-6.
K. M. Ryan et al., "Electric-Field-Assisted Assembly of Perpendicularly Oriented Nanorod Superlattices," Nano Letters, 2006, vol. 6, No. 7, pp. 1479-1482.
Wei-Jen Chen et al., "Functional Nanoparticle-Based Proteomic Strategies for Characterization of Pathogenic Bacteria," Analytical Chemistry. Dec. 15, 2008, vol. 80, No. 24, pp. 9612-9621.
D. A. Egas et al., "Fundamentals of Protein Separations: 50 Years of Nanotechnology, and Growing," Annual Review of Analytical Chemistry, 2008, vol. 1, pp. 833-855.
Y. Min et al., "The role of interparticle and external forces in nanoparticle assembly," Nature Materials, Jul. 2008, vol. 7, pp. 527-538.
X. Duan et al., "Single-nanowire electrically driven lasers," Nature, Jan. 16, 2003, vol. 421, pp. 241-245.
Z. Nie et al., "Self-assembly of metal-polymer analogues of amphiphilic triblock copolymers," Nature Materials, Aug. 2007, vol. 6, pp. 609-614.
M. Breunig et al., "Polymers and nanoparticles: Intelligent tools for intracellular targeting?" European Journal of Pharmaceutics and Biopharmaceutics, 2008, vol. 68, pp. 112-128.
J. L. Swift et al., "Nanoparticles as Fluorescence Labels: Is Size All that Matters?" Biophysical Journal, Jul. 2008, vol. 95, pp. 865-876.
H. M. E. Azzazy et al, "Nanodiagnostics: A New Frontier for Clinical Laboratory Medicine," Clinical Chemistry, 2006, vol. 52, No. 7, pp. 1238-1246.
T. Zhai et al., "Morphology-Dependent Stimulated Emission and Field Emission of Ordered CdS Nanostructure Arrays," American Chemical Society Nano Letters, 2009, vol. 3, No. 4, pp. 949-959.
J. Hu et al., "Linearly Polarized Emission from Colloidal Semiconductor Quantum Rods," Science, Jun. 15, 2001, vol. 292, pp. 2060-2063.
H. Htoon et al., "Light amplification in semiconductor nanocrystals: Quantum rods versus quantum dots," Applied Physics Letters, Jun. 30, 2003, vol. 82, No. 26, pp. 4776-4778.
C. O'Sullivan et al., "Gold tip formation on perpendicularly aligned semiconductor nanorod assemblies," Journal of Material Chemistry, 2008, vol. 18, pp. 5218-5222.
S. Coe et al., "Electroluminescence from single monolayers of nanocrystals in molecular organic devices," Nature, Dec. 2002, vol. 420, pp. 800-803.
A. Merkoçi, "Electrochemical biosensing with nanoparticles," The FEBS Journal, 2007, vol. 274, pp. 310-316.
J. Zhuang et al., "Cylindrical Superparticles from Semiconductor Nanorods," Journal of the American Chemical Society, 2009, vol. 131, pp. 6084-6085.
K. M. Ryan et al., "Control of Pore Morphology in Mesoporous Silicas Synthesized from Triblock Copolymer Templates," Langmuir, 2002, vol. 18, pp. 4996-5001.
J. S. Steckel et al., "Blue Luminescence from (CdS)ZnS Core-Shell Nanocrystals," Angewandte Chemie International Edition, 2004, vol. 43, pp. 2154-2158.
W. J. Park et al., "Biological applications of colloidal nanocrystals," Nanotechnology, 2003, vol. 14, pp. R15-R27.
Liang-shi Li et al., "Semiconductor Nanorod Liquid Crystals," Nano Letters, Jun. 2002, vol. 2, No. 6, pp. 557-560.
F. Gentile et al., "The Transport of Nanoparticles in Blood Vessels: The Effect of Vessel Permeability and Blood Rheology," Annals of Biomedical Engineeering, Feb. 2008, vol. 36, No. 2, pp. 254-261.
S. Ahmed et al., "Self-Assembly of Vertically Aligned Nanorod Supercrystals Using Highly Oriented Pyrolytic Graphite," Nano Letters, 2007, vol. 7, No. 8, pp. 2480-2485.
A. V. Kabanov et al., "Pluronic block copolymers as novel polymer therapeutics for drug and gene delivery," Journal of Controlled Release, 2002, vol. 82, pp. 189-212.
S. A. Empedocles et al., "Photoluminescence from Single Semiconductor Nanostructures," Advanced Materials, 1999, vol. 11, No. 15, pp. 1243-1256.
W. Jiang et al., "Nanoparticle-mediated cellular response is size-dependent," Nature Nanotechnology, Mar. 2008. vol. 3, pp. 145-150.
D. P. Kalogianni et al., "Nanoparticle-based DNA biosensor for visual detection of genetically modified organisms," Biosensors and Bioelectronics, 2006, vol. 21, pp. 1069-1076.
H. Liu et al., "Mechanistic Study of Precursor Evolution in Colloidal Group II-VI Semiconductor Nanocrystal Synthesis," Journal of the American Chemical Society, 2007, vol. 129, pp. 305-312.
J. K. Jaiswal et al., "Long-term multiple color imaging of live cells using quantum dot bioconjugates," Nature Biotechnology, Jan. 2003, vol. 21, pp. 47-51.
M. Brehm et al., "Infrared Spectroscopic Mapping of Single Nanoparticles and Viruses at Nanoscale Resolution," Nano Letters, Jul. 2006, vol. 6, No. 7, pp. 1307-1310.

* cited by examiner

PROCESSING OF NANOPARTICLES

This application has a priority of Irish no. 2009/0775 filed Oct. 5, 2009, and Irish no. 2009/0822 filed Oct. 23, 2009, hereby incorporated by reference.

FIELD OF THE INVENTION

This invention relates to processing of nanoparticles such as nanoparticles of a semiconductor material for example CdS, CdSe, or CdTe nano-rods.

PRIOR ART DISCUSSION

Close-packed semiconductor nanorod assemblies where each one-dimensional nanocrystal adopts a side by side ordering and uniform axial orientation are known. While discrete nanorods show polarized light emission, length dependent photon absorption, and high fluorescence cross-sections [1, 2], their collective assembly can allow scalable applications in next generation LEDs, photovoltaics, and field emission devices [3-10].

Nanorods have been directed into perpendicularly ordered assemblies either by using external electric fields or by evaporation control at solid-liquid or liquid-air interfaces [11-14] The aspect ratio and polydispersity of the rods in addition to solvent evaporation dynamics play a key role in achieving vertical alignment and close packing from solution. In effect, the gradual packing of randomly dispersed nanorods into a reducing solvent volume allows attractive dipole—dipole and van der Waals forces between ligand-capped nanorods to dominate the assembly behavior at a substrate [15]. Assemblies of nanorods dispersed in solution are also interesting in particular where individual properties such as linearly polarized emission can be collectively harnessed for example as novel fluorescent biomarkers [16-17]. In non-polar solvents, ligand capped nanorods are randomly dispersed in dilute solutions but can form nematic liquid crystal (LC) phases in more concentrated dispersions [18]. The LC behavior is dynamic and is destroyed outside of local temperature and concentration variations limiting discrete application. More robust and potentially biocompatible nanorod assemblies can be achieved when nanorods are stabilized in the aqueous phase as micelles. Nie et al. functionalized gold nanorods with hydrophilic CTAB ligands grafted along the rod sides with hydrophobic polystyrene on the rod ends which assembled into either discrete chains or spherical bundles depending on the water concentration in mixed DMF or THF solvent [19]. More recently, Zhuang et al. achieved water dispersible disc shaped CdS—CdSe nanorod assemblies in a two stage process by further co-ordinating individual alkyl capped nanorods with a dual interaction ligand (dithiol-functionalized Tween-20, Tween-SH) followed by annealing in ethylene glycol at 80° C. [20].

Much research effort has taken place to achieve simple and reliable synthesis of such particles so that they can be more usefully employed for applications such as biological markers in sample testing, next generation electronics and device storage.

The invention is directed towards achieving improved processing of nanoparticles for applications such as biological markers.

REFERENCES

1 J. Hu, L.-S. Li, W. Yang, L. Manna, L.-W. Wang and A. P. Alivisatos, Science, 2001, 292, 2060.
2 S. A. Empedocles, R. Neuhauser, K. Shimizu and M. G. Bawendi, Adv. Mater., 1999, 11, 1243.
3 A. P. Alivisatos, J. Phys. Chem., 1996, 100, 13226.
4 I. Gur, N. A. Fromer, M. L. Geier and A. P. Alivisatos, Science, 2005, 310, 462.
5 X. F. Duan, Y. Huang, R. Agarwal and C. M. Lieber, Nature, 2003, 421, 241-245.
6 N. C. Greenham, X. G. Peng and A. P. Alivisatos, Phys. Rev. B: Condens. Matter, 1996, 54, 17628.
7 J. S. Steckel, J. P. Zimmer, S. Coe-Sullivan, N. E. Stott, V. Bulovic and M. G. Bawendi, Angew. Chem., Int. Ed., 2004, 43, 2154.
8 S. Coe, W. K. Woo, M. Bawendi and V. Bulovic, Nature, 2002, 420, 800.
9 R. Xie, D. Battaglia and X. Peng, J. Am. Chem. Soc., 2007, 129, 15432.
10 T. Zhai, X. Fang, Y. Bando, Q. Liao, X. Xu, H. Zeng, Y. Ma, J. Yao and D. Golberg, ACS Nano, 2009, 3, 949.
11 K. M. Ryan, A. Mastroianni, K. A. Stancil, H. Liu and A. P. Alivisatos, Nano Lett., 2006, 6, 1479.
12 S. Ahmed and K. M. Ryan, Nano Lett., 2007, 7, 2480.
13 C. O'Sullivan, S. Ahmed and K. M. Ryan, J. Mater. Chem., 2008, 18, 5218.
14 C. C. Kang, C. W. Lai, H. C. Peng, J. J. Shyue and P. T. Chou, ACS Nano, 2008, 2, 750.
15 Y. Min, M. Akbulut, K. Kristiansen, Y. Golan and J. Israelachvili, Nat. Mater., 2008, 7, 527.
16 J. K. Jaiswal, H. Mattoussi, M. J. Mauro and S. M. Simon, Nat. Biotechnol., 2003, 21, 47.
17 W. J. Parak, D. Gerion, T. Pellegrino, D. Zanchet, C. Micheel, S. C. Williams, R. Boudreau, M. A. L. Gros, C. A. Larabell and A. P. Alivisatos, Nanotechnology, 2003, 14, R15-R27.
18 L.-S. Li, J. Walda, L. Manna and A. P. Alivisatos, Nano Lett., 2002, 2, 557.
19 Z. Nie and et al., Nat. Mater., 2007, 6, 609. 4
20 J. Zhuang, A. D. Shaller, J. Lynch, H. Wu, Ou. Chen, A. D. Q. Li and C. Y. Cao, J. Am. Chem. Soc., 2009, 131, 6084.
21 K. M. Ryan, N. R. B. Coleman, D. M. Lyons, J. P. Hanrahan, T. R. Spalding, M. A. Morris, D. C. Steytler, R. K. Heenan and J. D. Holmes, Langmuir, 2002, 18, 4996.
22 A. V. Kabanov, E. V. Batrakova and V. Y. Alakhov, J. Controlled Release, 2002, 82, 189.
23. H. Liu, J. S. Owen and A. P. Alivisatos, J. Am. Chem. Soc., 2007, 129, 305.
24. H. Htoon, J. A. Hollingworth, A. V. Malko, R. Dickerson and V. I. Klimov, Appl. Phys. Lett., 2003, 82, 4776.
25 U. Westedt, L. Barbu-Tudoran, A. K. Schaper, M. Kalinowski, H. Alfke and T. Kissel, AAPS PharmSciTech, 2002, 4, 206.
26 Nanoparticles in Biomedical Imaging Emerging Technologies and Applications In Fundamental Biomedical Technologies, ed., J. W. M. 5 Bulte and M. M. J. Modo, New York, USA, 2008, vol. 3, XVIII.
27. A. Merkoci, FEBS J., 2006, 274, 310.
28 F. Gentile, M. Ferrari and P. Decuzzi, Ann. Biomed. Eng., 2008, 36, 254.
29 Biofunctionalization of Fluorescent Nanoparticles, Nanotechnology in Biology and Medicine—Methods, Device and Application, Taylor & Francis Group, LLC, 2006. 6
30 J. L. Swift and D. T. Cramb, Biophys. J., 2008, 95, 865.
31 D. P. Kalogianni, T. Koraki, T. K. Christopoulos and P. C. Ioannou, Biosens. Bioelectron., 2006, 21, 1069.
32 W.-J. Chen, P.-J. Tsai and Y.-C. Chen, Anal. Chem., 2009, 81, 1722.
33 H. M. E. Azzazy, M. M. H. Mansour and S. C. Kazmierczak, Clin. Chem. (Washington, D.C.), 2006, 52, 1238.

34 M. Brehm, T. Taubner, R. Hillenbrand and F. Keilmann, Nano Lett., 2006, 6, 1307.
35 M. Breunig, S. Bauer and A. Goepferich, Eur. J. Pharm. Biopharm., 2008, 68, 112.
36 W. Jiang, B. Y. S. Kim, J. T. Rutka and W. C. W. Chan, Nat. Nanotech., 2008, 3, 145.
37 D. A. Egas and M. J. Wirth, Annu. Rev. Anal. Chem., 2008, 1, 833.

SUMMARY OF THE INVENTION

According to the invention, there is provided a method of processing nanoparticles comprising the steps of providing ligand-capped nanoparticles dispersed in an organic solvent; and performing phase transfer of the nanoparticles. Phase transfer may be by introducing into the organic solvent an aqueous solution of a polymer surfactant dissolved in water, and mixing the organic solvent and the aqueous solution until the polymer forms micelles which encapsulate the nanoparticles in assemblies.

Concentration of the polymer surfactant may be controlled to tune the assembly size. In another embodiment, temperature of the phase change reaction is controlled to tune the assembly size. In another embodiment, rate of mixing is controlled to tune the assembly size.

In one embodiment, separation is performed after phase transfer to provide assemblies of a desired size range.

In one embodiment, separation is performed after phase transfer to provide assemblies of a desired size range, and said separation comprises centrifuging.

In one embodiment, the polymer surfactant is a copolymer, such as a triblock copolymer. In one embodiment; the polymer surfactant is a triblock copolymer which is lyophilic with a hydrophobic head group and two hydrophilic tails, and in the aqueous solution the hydrophobic components organize to form a micelle with a hydrophobic core in the centre and a hydrated shell in contact with water.

In one embodiment, the polymer surfactant is a triblock copolymer which is lyophilic with a hydrophobic head group and two hydrophilic tails, and in the aqueous solution the hydrophobic components organize to form a micelle with a hydrophobic core in the centre and a hydrated shell in contact with water, and wherein the hydrophobic tails are of approximately equal length.

In one embodiment, the nanoparticles are nanorods.

In one embodiment, the nanoparticles are nanorods covered with long-chain alkyl ligands which are hydrophobic and are compatible with a micelle core and are trapped there on phase transfer, in which a reduced volume of the core causes a close-packing of the nanorods into assemblies with sizes governed by the size of the micelle.

In one embodiment, the mixing comprises stirring with a stirring rate of about 50 rpm to about 500 rpm.

In one embodiment, the nanoparticles are formed from a semiconductor material, such as one or more of CdS, CdSe and CdTe.

In one embodiment, the nanoparticles are formed from a metal, such as one or more of Cu, Fe, Ag and Au.

In one embodiment, the organic solvent is toluene.

In one embodiment, the polymer is a copolymer selected from one or more of pluronic F127, F88, P123 and P65. In one embodiment, the polymer is a copolymer present at a concentration of between about 1% to about 20% (w/v) more preferably about 2% to 4% (w/v).

In one embodiment, the nanoparticle assemblies have a size of between about 20 nm to about 500 nm.

In one embodiment, the nanoparticle assemblies are separated after phase transfer by filtration, and may be filtered through a filter with a pore size of about 0.4 µm to 3.0 µm.

In another aspect, the invention provides an encapsulated assembly of nanoparticles in an aqueous medium.

In one embodiment, the assembly is encapsulated by a polymer. In one embodiment, said polymer is a triblock copolymer, which for example may be selected from one or more of pluronic F127, F88, P123 and P65. The copolymer may be present at a concentration of between about 1% to about 20% (w/v), more preferably about 2% to 4% (w/v).

In one embodiment, the nanoparticles are of a semiconductor material, such as one or more of CdS, CdSe and CdTe.

In one embodiment, the assembly has a size of between about 10 nm and 200 nm, preferably about 20 nm to about 80 nm.

In one embodiment, the nanoparticles are nanorods and the assembly is anisotropic.

In a further aspect, the invention provides a biomarker comprising an encapsulated fluorescent nanoparticle assembly in an aqueous medium. The assembly of the biomarker may have any of the characteristics given above.

In another aspect, the invention provides use of a nanorod assembly as defined above as a biomarker. The biomarker may be an intracellular biomarker.

DETAILED DESCRIPTION OF THE INVENTION

Brief Description of the Drawings

The invention will be more clearly understood from the following description of an embodiment thereof, given by way of example only, with reference to the accompanying drawings, in which.

DESCRIPTION OF THE EMBODIMENTS

Figure 1:
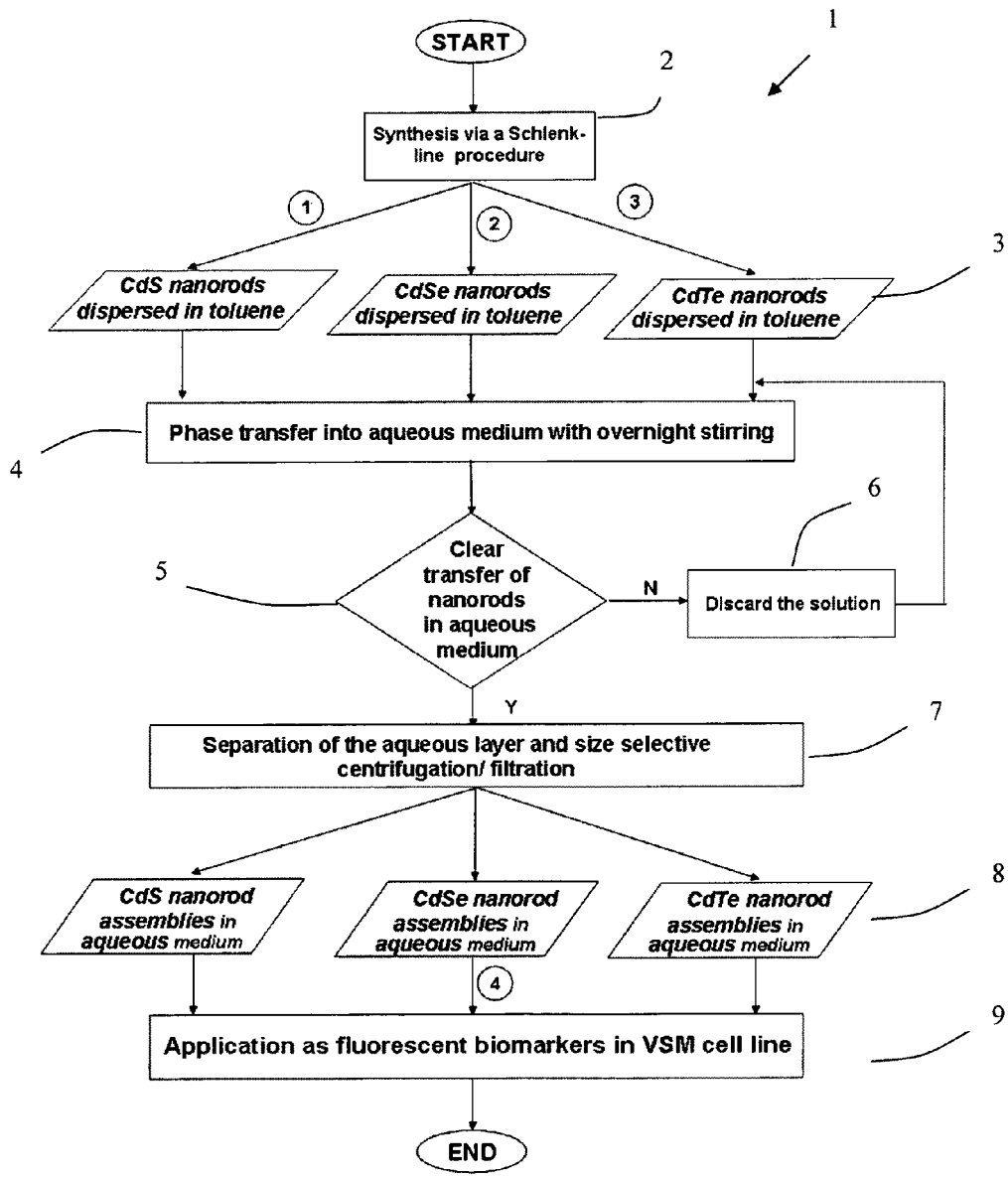
FIG. 1 is a flow diagram illustrating a method of the invention for processing CdS, CdSe, and CdTe nano-rods to provide fluorescent bio-markers.

We have devised a method for producing nanoparticle assemblies in an aqueous medium. The nanoparticles may be nanorods, but they could alternatively be in spherical form for example. The application may be for example as bio markers. The assemblies may have a number of nanoparticles in a size range of tens to thousands. The fact that the nanoparticles are in size tunable assemblies in an aqueous medium provides the advantages of tailoring the assembly size to the desired application such that their collective emission for example can act as a brighter biological tag In the method, ligand-capped nanoparticles are dispersed in an organic solvent. There is then phase transfer of the nanoparticles introducing into the organic solvent an aqueous solution of polymer surfactant dissolved in water. The organic solvent and the aqueous solution are then mixed until the polymer forms micelles which encapsulate the nanoparticles in assemblies. The resultant nanoparticle assemblies in an aqueous phase may be used for any of a range of desired applications. It has been found that the assembly size can be tuned by control of any or a combination of method parameters such as:

concentration of polymer surfactant, and/or
temperature of the phase change reaction, and/or
rate of mixing, such as rotational rate of stirring.

The nanoparticle assemblies may be for example water soluble NRSCs of CdS, CdSe and CdTe. A phase transfer occurs at room temperature with the encapsulation and close packing of a group of nanorods in the hydrophobic core of a triblock copolymer micelle. The method of transfer is generally applicable to any monodisperse solution of ligand capped nanorods or nanoparticles. The order and axial alignment of the assemblies in the case of rods allows discrete nanorod properties such as fluorescence to be enhanced by collective emission. Uptake of the water dispersible nanorod ensembles in a cell line showed strong membrane and cell specific fluorescence at low laser intensity. The range of sizes (50-600 nm) obtainable with water dispersible nanorod assemblies and the biocompatibility of their polymer shells have the potential to greatly extend both the range and diversity of biological applications possible with semiconductor nanocrystals.

We describe a single-step route which is typically carried out at room temperature (although ranges from 15-55 C were also investigated with higher temperatures leading to a larger micelle radius in a typical embodiment) to the formation of water dispersible nanorod assemblies of CdS, CdSe and CdTe using triblock copolymer surfactants of the form PEOxPPOy-PEOx (PEO: polyethylene oxide, PPO: polypropylene oxide). These types of copolymers are known to self-assemble to form morphological variations of spherical, vesicular or mesophasic aggregates in aqueous solutions and are widely used in the pharmaceutical industry to solubilise hydrophobic drugs [21, 22] Here, we demonstrate that stirring an organic solution of alkyl capped nanorods mixed with an aqueous solution of the triblock copolymer results in the formation of very stable aligned nanorod assemblies in the aqueous phase. The phase transfer occurs whereby discrete alkyl capped nanorods in the organic phase are transferred to the aqueous phase via encapsulation in hydrophobic polypropylene oxide core of a triblock micelle. On phase transfer, the randomly dispersed nanorods in the organic medium close pack in the form of discs encapsulated in the hydrophobic core of water dispersible micelles. The triblock copolymer is lyophilic with a hydrophobic head group and two equal length hydrophilic tails. In an aqueous solution the hydrophobic components organize to form a micelle with a hydrophobic core in the centre and a hydrated shell in contact with water. As the nanorods are covered with long-chain alkyl ligands which are hydrophobic they are compatible with the core of the micelle and get trapped there on phase transfer. The reduced volume of the core causes a close-packing of the nanorods/nanoparticles forming close packed assemblies with sizes tuned by the size of the micelle. The resultant close packed disk shaped assemblies consists of rods tethered only by the interdigitation of the original long chain alkyl ligands suggesting the triblock copolymer does not co-ordinate to each individual nanorod but to the rod ensemble. In vitro analysis showed an excellent uptake of the water dispersed nanorod assemblies by human vascular smooth muscle cell and the occurrence of various spectral properties via this interaction (membranous and intracellular) demonstrates their potential as fluorescent labels.

Figure 2:
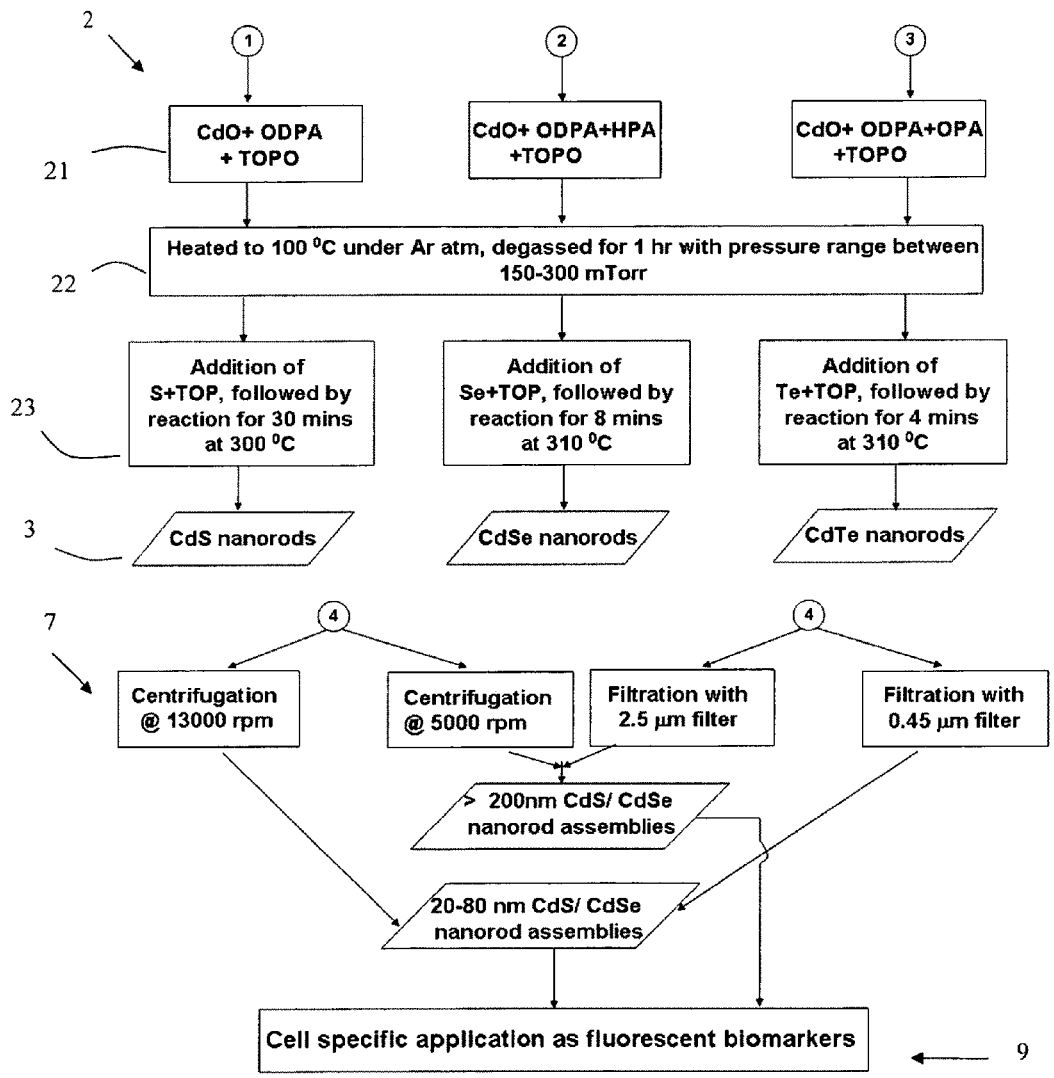
FIG. 2 is a flow diagram illustrating synthesis and separation steps of the method in more detail.

Referring to FIGS. 1 and 2 in a method 1 of processing nanoparticles a Schlenk—line procedure is used in a step 2 to provide CdS, CdSe, and CdTe nano-rods 3 dispersed in toluene. In a step 4 there is phase transfer into aqueous medium with overnight stirring. A decision step 5 indicates if there has been clear transfer of nano-rods in the aqueous medium, and solvent phase is discarded in step 6. In step 7 there is separation of the aqueous layer and size-selective centrifugation to provide Cds, CdSe, and CdTe nano-rod assemblies 8 in the aqueous medium. In step 9 the nano-rod assemblies can be used as fluorescent bio-markers for example in a vascular smooth muscle (VSM) cell line.

FIG. 2 shows the synthesis step 2 in more detail—comprising a reaction step 21 and a heating step 22 followed by a further reaction steps 23 to provide the nano-rods 3.

FIG. 2 also shows the separation step 7 in more detail: including centrifugation and filtration. It is not essential for the invention that there be separation, however, it is advantageous for many applications as it provides graded sizes of assemblies. Judicious size selection of the Nanorod Super-Crystals (NRSCs) was achieved through centrifugation by sequentially increasing the speed with the largest disc greater than about 200 nm precipitating at about 5500 rpm and the smallest assemblies (between about 20 to about 80 nm) precipitating at about 13000 rpm. Filtration may be applied as an alternative separation protocol, for example, the aqueous solution of phase transferred CdS NRSCs may be filtered through two different pore size filter papers, the first one may be Whatman grade 5 (pore size approximately 2.5 micron) and the second one may be Millipore (pore size approximately 0.45 micron). TEM analysis of the filtrate revealed separation of larger NRSCs when the aqueous phase salutation was filtered through a pore size of about 2.5 micron whereas smaller assemblies (from between about 40 to about 100 nm) could be easily separated by filtering the aqueous phase solution through a membrane with a pore size of about 0.45 micron. NRSCs between about 300 to about 400 nm can be easily transported in the blood vessel and capillary system. NRSCs in the about 100 to about 300 nm range have promising applications in bio-imaging techniques such as cardiovascular pathology, biosensors, liquid chromatography and bio-separation methods. NRSC assemblies in the about 30 to about 100 nm range may be smaller than the target species but can specifically interact with different biological entities for example a protein (typical size range between about 5 to about 50 nm), a virus (typical size range between about 20 to about 500 nm), or a gene (typically about 2 nm wide and between about 10 to about 100 nm long) and may find use in applications such as FRET analysis, hybridization or nanoscale analysis of low abundant proteins and peptides (nanoproteomics).

The invention will be more clearly understood from the following examples.

EXAMPLES

Materials

Cadmium oxide (>99%) was purchased from Fluka, trioctylphosphine (TOP, 90%), tri-n-octylphosphine oxide (TOPO, 99%), sulfur (99.98%), selenium (99.98%) and tellurium (99.98%) were purchased from Aldrich. n-Octadecylphosphonic acid (ODPA), n-tetradecylphosphonic acid (TDPA), n-hexylphosphonic acid (HPA), and n-octylphosphonic acid (OPA) were obtained from PolyCarbon Industries, Inc. (PCI). The block copolymers F88, F127, P123, and P65 were obtained from BASF, Germany. All the chemicals were used as received. Filter paper of pore sizes 2.5 micron and 0.45 micron was purchased from Whatman and Millipore Corporation, respectively, for size selective separation of the nanorod assemblies through filtration.

Characterization

Transmission electron microscopy (TEM) was performed using a JEOL 2011 TEM operating at an accelerating voltage of 200 kV. Selected area electron diffraction (SAED) was also observed from the regions of perpendicularly aligned CdS nanorods. UVVis spectroscopy and fluorescence measurements of the phase transferred solutions were carried out on a Cary-300 Bio UV-Vis spectrophotometer operated at a resolution of 1 nm and a Varian Cary Eclipse Fluorescence Spectrophotometer, respectively. XRay photoelectron spectroscopy (XPS) measurement of the phase transferred nanorods was carried out in a Kratos Axis 165 spectrometer using monochromated Al Ka radiation (hn ¼ 1486.58 eV). High resolution spectra were taken for the following photoelectron transitions: Cd3d, S2p, O1s and C1s at a fixed analyser pass energy of 20 eV. The core level spectra were background corrected using the Shirley algorithm and the chemically distinct species were resolved using a mixed Gaussian-Lorentzian fitting procedure. The core level binding energies (BEs) were calibrated using C1s at 284.8 eV. To investigate the mechanism of the phase transfer process, a drop of the phase transferred CdS nanorods by F127 was observed on a clean glass slide under an optical microscope (Model: Axio Imager MAT, Carl Zeiss AG Light microscopy). Confocal microscopy was performed on "Carl-Zeiss Meta 710" instrument excited with a 405 nm laser. Scanning electron microscopy (SEM) of the phase transferred samples, drop-cast on a Si (111) substrate was performed by a Hitachi S-4800 machine. Localization of nanoparticles was performed using a spectral laser scanning microscope Meta 710 based on the Axio Observer II (Carl Zeiss, Germany) equipped with a Zeiss Neofluor 20× objective. Excitation wavelengths were 405 nm and 488 nm. All confocal images were acquired with the same settings with respect to laser intensity and detector gain. Optical sectioning was performed to obtain the pattern of spatial distribution nanorods (cell surface, intracellular compartments).

Example 1

Synthesis of CdS Nanorods

This example illustrates the preparation of CdS NRSCs ranging from 100-600 nm by phase transfer of as-prepared CdS nanorods from a toluene (organic) phase to an aqueous phase. The CdS nanorods utilised in this study were synthesised essentially through the pyrolysis method, redispersed in toluene and kept under a $N_2$ environment inside a glove-box. In a typical experiment about 800 µL of sulphur-tri-octylphosphine mixture was injected to a hot mixture of cadmium oxide and surfactants ODPA and TOPO (1:2:>4 by molar ratio respectively) at a temperature of about 300° C. The reaction was quenched after about 30 mins by adding a suitable quantity of toluene. A stoichiometric amount of acetone was added to precipitate the nanorods (average length and diameter around 25-30 nm and about 6-8 nm respectively), following which they were centrifuged and redispersed in toluene.

Phase Transfer

About 5 ml each of 3% of the block copolymers a) F127, b) F88, and c) P65, (obtained from BASF Germany) was mixed separately with 5 ml of the diluted CdS nanorods in toluene and was allowed to stir intensively for about 12 hrs until there was a clear observation of an appearance of color in the aqueous phase. The top organic layer from the three samples was carefully separated and later discarded. The remaining aqueous layer was centrifuged and washed a couple of times with deionised water in order to remove excess unbound surfactants. Aliquots from these resulting solutions were taken and used for further characterizations (TEM and SEM images, photographs of glass vials in FIGS. 2 to 5). Table 1 below shows the result of the phase transfer with the individual block copolymers.

TABLE 1

Result of phase transfer of CdS nanorods with change in block copolymers

| Block copolymer | Hydrophobic Polypropylene oxide chain length | Hydrophilic Polyethylene oxide chain length | Phase Transfer with comments |
|---|---|---|---|
| F127 | 69 units | 106 units | Yes, quick and most effective |
| F88 | 39 units | 102 units | Yes, with time and slight formation of emulsion at the interface |
| P65 | 30 units | 20 units | No, formation of emulsion, not separable |

In an alternative phase transfer method, 5 ml of 3% block copolymers (Pluronic F88, F127, P123, and P65, obtained from BASF, Germany) were mixed with 5 ml of the diluted CdS nanorods in toluene and allowed to stir intensively for 12 h until there was a clear observation of an appearance of color in the aqueous phase. The top organic layer was carefully separated and later discarded. The remaining aqueous layer was centrifuged and washed a couple of times with de-ionized water in order to remove excess unbound surfactants. Aliquots from these resulting solutions were taken and used for further characterization. Phase transfer was accomplished with 5% and 20% F88 in the same manner.

Figure 6:
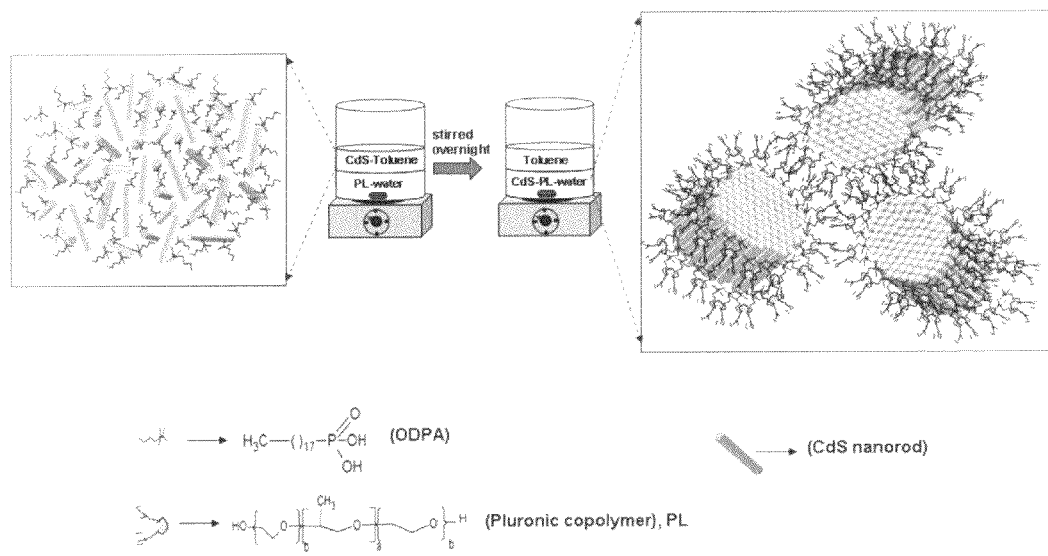
FIG. 6 is a set of diagrams illustrating a reaction mechanism pathway.

FIG. 6 represents a schematic of the possible reason of formation of these assemblies where the phase transfer occurs by the aggregation and encapsulation of individual alkyl capped nanorods as a hydrophobic core most likely co-ordinated to a polypropyl oxide (PPO) corona and polyethylene oxide (PEO) shell of a triblock copolymer micelle. It is anticipated that there are two factors responsible for the phase transfer of CdS nanorods from toluene to water and thereby resulting into assemblies, namely (1) hydrophobic-hydrophobic interaction between hydrophobic head groups of the copolymer and the long chain hydrocarbon of ODPA capping ligands on the CdS nanorods and (2) the hydrophilic tail of the copolymer should be sufficient to provide a good hydrophilic environment to the compact micelle like structure. We found that the mere presence of a large hydrophobic head or a large hydrophobic tail is insufficient for proper phase transfer. Among the set of four different triblock copolymer used in the experiment, F127 has the longest head and tail. So both the factors are applicable in this case, enabling a good protection to the hydrophobic core as well as providing a good hydrophilic environment, thus F127 worked best in generating nanorods assemblies. F88 has equivalent long hydrophilic tails like F127 but the head group is relatively small. Thus factor (1) is relatively weak and is not enough for an effective phase transfer. Therefore a lower concentration of F88 is not sufficient for 100% phase transfer, but on increasing the F88 concentration, the number of molecules interacting with CdS increases and as a result phase transfer capability was enhanced. The tail of the copolymer F88 was long and thus able to make the NRSC water dispersible without any difficulty. P123 has a long hydrophobic head, so it can also successfully phase transfer CdS to water and satisfy factor (1), but the short hydrophilic tail is responsible for its poor water dispersibility. For similar reasons phase transfer by P65 does not occur due to the combination of short head (PPO) as well as short tail (PEO). A unique feature of these assemblies as shown in the TEM images of FIG. 3G, FIG. 4 is that each consists of an ensemble of axially aligned and close packed CdS, CdSe nanorods. The inter-rod distance of the phase transferred nanorods was found to be about 3.5 nm which was comparable when individual rods were vertically aligned by external methods in the organic medium. This in a way proves that the copolymer interacts with the bunch as a whole and not with the individual nanorods.

Cellular Uptake of CdS Nanorods

Figure 7:
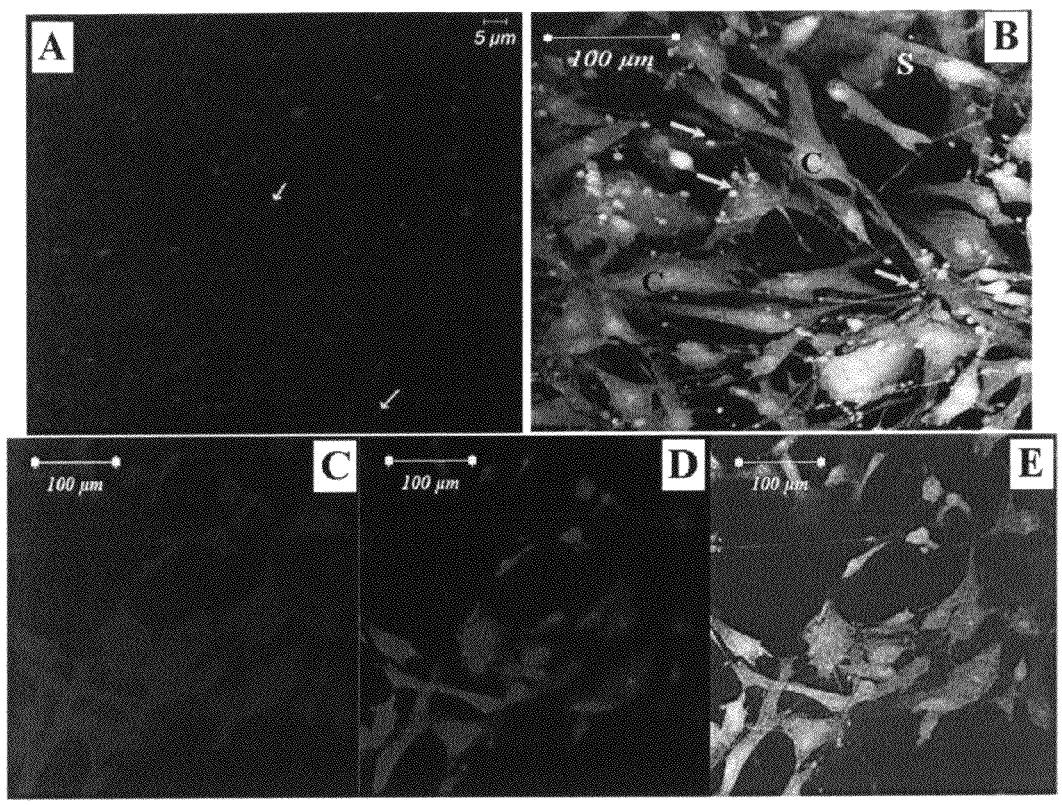
FIGS. 7(a) to (e) are images for investigation of cellular bio-compatibility.

Vascular Smooth Muscle Cells (VSMC) (PromoCell, Germany) were grown in monolayers at 37° C. in a humidified atmosphere at 5% $CO_2$ in 5% Fetal Bovine Serum—VSMC media supplemented with penicillin/streptomycin. At about 85% confluence, cells were detached from a 75 $cm^2$ flask surface by treatment with 0.25% trypsin and a 0.02% EDTA in $Ca^{2+-}$ and $Mg^{2+-}$ free PBS (pH 7.3). Cells were plated for about 24 h before the experiment on poly-L-lysine-coated glass cover slips at $5 \times 10^3$ cell/$cm^2$. After incubation for about 12 hours with CdS nanorods/VSMC media at 37° C. in a humidified 5% $CO_2$ incubator, cells were washed three times with PBS in order to remove any loosely attached or non-attached nanorods and then fixed in a 4% formaldehyde solution in PBS at room temperature for about 10 min. The cells were then washed twice with PBS and incubated with 0.1% Triton X-100 (Sigma-Aldrich) plus 1% bovine serum albumin (BSA; Sigma-Aldrich) in PBS at room temperature for 15 min followed by 5 µg/ml 4',6-diamidino-2-phenylindole (DAPI; Molecular Probes) staining in PBS for 3 min at room temperature. The slides were washed twice with PBS, mounted with glycerol on the glass slide for microscopical observation (FIG. 7).

Preliminary investigation of biological application was carried out by in vitro analysis in a human vascular smooth muscle (VSM) cell line which is a primary candidate for biomedical treatment for many cardiovascular pathologies [25]. Excitation ($\lambda$=405 nm) of the phase transferred CdS NRSCs by CLSM (confocal laser scanning microscope, FIG. 7A) yielded a characteristic fluorescence intensity in the blue and further confirmed the ease of dispersibility and homogeneous size distribution of the disc shaped assemblies (200-600 nm range). The VSM cell line was incubated with the NRSCs and their internalization, cellular uptake and intracellular distribution were further monitored. Uptake occurred without any transfection agents into the adherent VSM cell line and was efficient, fast and led to high loading into the cells, FIGS. 7B and E. Rapid and irreversible internalization starts during the first 20 min of incubation with no excretion or further aggregation even after 24 h. With application of optical sectioning we were able to show two types of interaction between the cells and NRSCs: adsorption of the nanostructures on the cell membrane giving membranous fluorescence in the blue spectral region, FIG. 7C and internalization of the NRSCs inside the cell giving intracellular fluorescence in the red spectral region, FIG. 7D. Overall, there is a significant fluorescence intensity signal from NRSC treated cells (FIG. 7B-E) which allowed visualization of all minor structural details of cell shape, cell surface morphology and adhesion to substrate. Strong fluorescence, cellular uptake and prolonged persistence in the human cells (up to 7 days in this study) make these ensembles potentially useful as fluorescent probes in a range of biological applications including for example flow cytometry techniques, cell-scaffold interaction studies and DNA markers [26, 27]. Similar results were obtained with several other cell lines like mouse fibroblasts "Primo Cells" and human vascular endothelial cells. Water soluble NRSCs may have advantages over discrete nanorods in that the total intensity of emission is proportional to the number of rods and their size can potentially be tuned to specifically match different biological entities for example a protein (5-50 nm), a virus (20-500 nm), or a gene (2 nm wide and 10-100 nm long). As an example, larger 300-400 nm NRSCs, while difficult to translocate to cell compartments, would still be small enough to transport in the blood vessel and capillary system [28]. NRSCs in the 100-300 nm range may have promising applications in imaging techniques of cardiovascular pathology, biosensors, liquid chromatography and bioseparation methodology [29-33]. Since the NRSCs in this size range would be larger than the targeted species, they most likely would participate in binding without significant perturbation of the binding equilibrium and provide an efficient detection of a low amount of a target by microscopy or spectroscopical tools [34, 35]. Assemblies in the 30-100 nm range will be similar in size or smaller than the target species and may find use in applications such as FRET analysis [36], hybridization or nanoscale analysis of low abundant proteins and peptides (nanoproteomics).

Example 2

Synthesis of CdSe Nanorods

This example demonstrates the preparation of CdSe Nanorod SuperCrystals (NRSCs) ranging in size from about 20 to about 300 nm by phase transfer of as-prepared CdSe nanorods from the toluene (organic) phase to the aqueous phase. The general approach for the synthesis of nanorods involves the stepwise addition of Cadmium precursor and followed by chalcogenide precursor at a high temperature. Briefly, CdO (0.2 g) as a cadmium precursor was dissolved in a mixture of surfactants for example n-tetradecylphosphonic acid (TDPA, 0.71 g), n-hexylphosphonic acid (HPA, 0.160 g) and tri-n-octylphosphine oxide (TOPO, 3.00 g) in a 25 ml three-neck flask equipped with a condenser and a thermocouple adapter. The mixture was heated to about 120° C. in an atmosphere of Ar and then degassed for about 60 min with pressure range between about 150 to about 300 mTorr and followed by heating at 300° C. under Ar atmosphere, during which the CdO decomposed and gave an optically clear solution. Once a clear solution was achieved, 1.5 g of trioctylphosphine (TOP) was added to the mixture and the temperature was further raised to 310° C. Next a stock solution of Selenium (about 500 µl) containing 0.073 g of selenium in 0.416 g of TOP was injected rapidly to the vigorously stirring precursors and the resulting particles were allowed to grow for about 5-10 min at 310° C. The growth of nanorods was terminated by removal of the heating mantle, and at about 80° C. between about 2 to about 4 ml of anhydrous toluene was added to the mixture to quench the reaction. The nanorods were purified by dissolution in toluene and precipitation from anhydrous isopropanol. They were cleaned thrice with a toluene and isoproponal mixture and redispersed in toluene for further measurements.

Phase Transfer 5 ml of 3 wt % in water of the block copolymers obtained from BASF Germany (Pluronic F88, F127, P123 and P65) were mixed separately with 5 ml of the diluted CdSe nanorods in toluene and allowed to stir intensively for about 12 hrs until there was a clear observation of an appearance of color in the aqueous phase. The top organic layer was carefully separated and later discarded. The remaining aqueous layer was centrifuged and washed a couple of times with deionised water in order to remove excess unbound surfactants. Aliquots from this solution were taken and used for further characterizations. Phase transfer was accomplished with 5% and 20% F88 in the same manner. CdSe nanorods dispersed in toluene were also phase transferred with 3% F127 and treated in a similar manner prior to characterisation. Fine tuning of the percentage weight of the surfactant in water also had an effect on micelle size within a 1% to 2% variation.

It is evident from the TEM images (FIG. 4) that the NRSCs of similar size can further organise on a larger scale into a pseudo-hexagonal arrangement that mimics the close packing of individual rods within each super crystal. This is yet another distinctive feature of the fact that the size of the NRSCs could be controlled through a judicious size selection procedure by sequentially increasing the centrifugation speed with the largest NRSCs (about 200 nm or more) precipitating at about 5500 rpm (FIG. 4D) and the smallest NRSCs (between about 20 to about 80 nm) precipitating at about 13000 rpm (FIG. 4E). The smallest NRSCs which form a discernable disc from the axial alignment and close packing of nanorods were typically between about 40 to about 50 nm in diameter, (FIG. 4F). Size selective precipitation could also be obtained by filtration using different pore size filters. Separation through filter paper pore size of about 2.5 micron, resulted in the appearance of larger assemblies of greater than about 200 nm in the TEM analysis, whereas most of the larger NRSCs were found to be trapped on the Millipore filter paper having about 0.45 micron pore size. Thus precise control over the size of the nanorod assemblies could be achieved which is a unique feature as each size domain can be used for specific biological target species.

Example 3

Synthesis of CdTe Nanorods/Dipods/Tetrapods

This example demonstrates the formation of CdTe nanorod assembly by phase transfer of as-prepared CdTe nanorods from the toluene (organic) phase to the aqueous phase. CdTe was also synthesised in a procedure exactly similar to that of CdSe. Here in this example, ODPA (0.812 g), TOPO (2.65 g), OPA (0.315 g) was used along with CdO. Tellurium stock solution (about 500 µl) containing 0.061 g of tellurium in 0.552 g TOP was rapidly injected (at a speed of less than 1.0 s) to the vigorously stirring Cd solution and particles were allowed to grow for about 4 minute at 310° C. The concentration of CdTe tetrapods and dipods were more than the nanorods in the resultant product. The particles were cleaned thrice with a toluene and methanol mixture and redispersed in toluene for further measurements.

Phase Transfer 5 ml each of 3% of the block copolymers obtained from BASF Germany (Pluronic F88, F127, P123 and P65) were mixed separately with 5 ml of the diluted CdTe nanorods/tetrapods in toluene and allowed to stir intensively for about 12 hrs until there was a clear observation of an appearance of color in the aqueous phase. The top organic layer was carefully separated and later discarded. The remaining aqueous layer was centrifuged and washed a couple of times with deionised water in order to remove excess unbound surfactants. Aliquots from this solution were taken and used for further characterizations. Phase transfer was also accomplished with 5% and 20% F88 in the same manner CdTe dipods/tetrapods dispersed in toluene were also phase transferred with 3% F127 and treated in a similar manner prior to characterisation.

Example 4

Functionalization of Assemblies

Assembled nanoclusters may be functionalized with biological and chemical agents/groups using different chemical, physical and/or biochemical methods. For example:

- Assemblies may be functionalized using hydrophobic interactions between a biological/chemical agent and the surface of nanoclusters.
- Assemblies may be functionalized using nonspecific absorption of biological/chemical agents on the nanoclusters.
- Assemblies may be functionalized using polymerization/cross-linking techniques between a biological/chemical agent and the nanocluster.
- Assemblies may be functionalized using electrostatic affinities between a biological/chemical agent and the nanocluster.
- Assemblies may be functionalized using ionic interaction between a biological/chemical agent and the nanocluster.

Assemblies may be functionalized using covalent or non-covalent bonds between a biological/chemical agent and the nanocluster.

Assemblies may be functionalized by enzymatic reaction (human, animal, fungal or bacterial enzymes) between a biological/chemical agent and the nanocluster.

It will be appreciated that a combination of two or more different functionalization techniques may be used to provide multi-functionalized nanorod assemblies.

It will be understood that the term "biological and chemical agents/groups" as used herein includes: pharmaceutical compounds, drug molecules, therapeutic compounds, radioactive compounds, chemotherapy agents, nucleic acids, antibodies, proteins, peptides, MRI contrast agents, preservatives, flavor compounds, smell compounds, colored dye molecules, fluorescent dye molecules, enzyme molecules, pesticides, fungicides and fertilizers, another nanoparticles, bacteriophages, animal viruses, antimicrobial agents, activator of cell receptors, an adjuvant that enhances immune response to the antigen, materials that enhance the incorporation of genetic material or stimulate the immune response, immunosuppressant, natural polymers, hormones and steroids, chemotherapeutics, antibiotics, antifungal agents, anesthetics, immunomodulators, anti-inflammatory drugs, pain relieving drugs, autonomic drugs, cardiovascular-renal drugs, endocrine drugs, hematopoietic growth factors, blood lipid lowering drugs, antileptics, and psychoactive drugs, aptamers, oligonucleotides, chemotherapeutics (anti-cancer drugs), antibiotics, antifungal agents, anesthetics, immunomodulators (e.g., interferon, cyclosporine), anti-inflammatory and other types of pain relieving drugs, autonomic drugs, cardiovascular-renal drugs, endocrine drugs, hematopoietic growth factors, blood lipid lowering drugs, AIDS drugs, modulators of smooth muscle function, antileptics, psychoactive drugs, and drugs that act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species, cytokines, ribozymes, interferons, oligonucleotide sequences that inhibit translation or transcription of other genes, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth hormones such as human growth hormone and its derivatives such as methione-human growth hormone and des-phenyla-lanine human growth hormone, human and animal growth hormone, fertility inhibitors such as the prostaglandins, fertility promoters, growth factors such as insulin-like growth factor, coagulation factors and anticoagulation factors, Non-steroidal anti-inflammatory drugs (NSAIDs), and combinations thereof.

Assembled CdS nanoclusters as described herein exhibit benefits for their practical utilisation and may provide a sufficient control over functionalization (biological and chemical agent and groups) due to their compactness, high density per volume, determined orientation and order within the cluster which may provide a major advantage in the biological applications of these assembled nanorods instead of non-assembled nanorods which are characterized by chaotic positioning within a sample.

Nanorod assemblies may be functionalized simultaneously using the unique chemical and physical characteristics of both the structural components: for example, for CdS, DNA and RNA incorporation and Gene and siRNA delivery and release may be possible based on the charge distribution and Pluronic polymers also can be functionalized with peptide chain, bioactive protein, enzymes, antibodies, liposomes, and pharmaceutical compounds of various nature and action.

For semi-conductor material nanorod assemblies, in particular CdS nanorod assemblies, we have found that charge distribution functionalization of the nanorod assemblies is possible because of the unique three-dimensional confinement of charge carriers within the assemblies. The characteristics (positive, negative, neutral) and type of the charge distribution may vary in strength possible because as a result of the number of nanorods and the organised positioning of CdS within assemblies.

Functionalized nanorod assemblies may be used in one or more of the following applications: nanomedical science, sensing, imaging, therapeutics, cellular physiology studies, tissue-engineering application, analysis and modulation of cell-scaffold interaction, cell line engineering, real-time imaging both in vivo, in vitro, for biotechnology application and various bioprocesses on various scales.

Cell-Targeted Delivery of Anti-Inflammatory Drug by Bi-Functionalized Nanoassemblies Assemblies of nanorods were prepared as described in Examples 1 to 3 above and were functionalized by covalently binding antibodies to the human endothelial cell surface protein, vascular cellular adhesion molecule 1 (VCAM-1) to the nanorod assemblies, a second functional agent such as a fluorescent lipophillic anti-inflammatory drug may be loaded on the assemblies using hydrophobic interaction. Human umbilical vein endothelial cells (HUVECs) (obtained from Promocells) were grown as monolayers in EGM (Endothelial Cell Medium with 2% fetal bovine serum (FBS), growth factors, antibiotic-antimycotics, and supplements from Clonetics) at 37° C., in humidified air and 5% $CO_2$ on sterile fibronectin coated glass coverslip placed on the bottom of the 6-well culture plate. When the cells were approximately 80-90% confluent, stimulation of the expression of the VCAM-1 on the cell surface was performed by adding pro-inflammatory stimulants TNF-α (250 U/ml) and IL-1α (50 U/ml) to the culture media. 12 hours following stimulation functionalized nanorod assemblies experiments were conducted as follows.

Serially-diluted functionalized nanorod assemblies (either control or functionalized) were incubated in 2 mL of phenol red-free medium with presence of the stimulated and non stimulated HUVECs for 30 to 60 minutes prior to washing with phosphate-buffered saline solution and replacing the nanoassemblies containing medium with phenol red-free medium without nanoparticles. Within 1-2 hour of exposure to the nanorod assemblies, the cells were viewed under a Zeiss AxioObserver fluorescent microscope.

The rate of drug delivery and specificity of drug distribution within cellular compartments may be observed using a Confocal laser scanning fluorescent microscope.

Delivery of Anti-Inflammatory Drug.

Nanorod assemblies were prepared as described in Examples 1 to 3 above. The nanorod assemblies were functionalized with a fluorescent hydrophobic anti-inflammatory drug (for example, praziquantel) using hydrophobic interaction.

Human umbilical vein endothelial cells (HUVECs) (obtained from Promocell) were grown as monolayers in EGM (Endothelial Cell Medium with 2% fetal bovine serum, growth factors, antibiotic-antimycotic, and supplements from Clonetics) at 37° C. in humidified air and 5% $CO_2$ on sterile glass fibronectin coated coverslip placed on the bottom of a 6-well culture plate. When the cells were approximately 80-90% confluent, stimulation of the pro-inflammatory response was performed by exposing the cells to TNF-α (250 U/ml) and IL-1α (50 U/ml). Following 12 hours of stimulation functionalized nanorod assembly experiments were conducted as follows.

Serially-diluted functionalized nanorods assemblies were incubated in 2 ml of phenol red-free medium in the presence of stimulated and non-stimulated HUVECs for 30 to 60 minutes prior to washing with phosphate-buffered saline solution and replacing the assemblies-containing medium with phenol red-free medium not containing nanorods. Within 1-2 hour of exposure cell to the assemblies, the cells were viewed under a Zeiss Observer fluorescent microscope.

The rate of drug delivery, internalisation and cellular location of the delivered can be observed using a Confocal laser scanning fluorescent microscope to visualize fluorescent drug molecules within HUVECs. Activity of the drug, and its inhibitory action on the pro-inflammatory cytokine cascade can be confirmed using RT-PCR analysis of mRNA expression of VCAM-1 of HUVEC compare to control cells (non-treated with assemblies however stimulated by TNF-α (250 U/ml) and IL-1α (50 U/ml), treated with non-functionalized assemblies and stimulated with TNF-α (250 U/ml) and IL-1α (50 U/ml), non stimulated with TNF-α (250 U/ml) and IL-1α (50 U/ml)).

Figure 8:
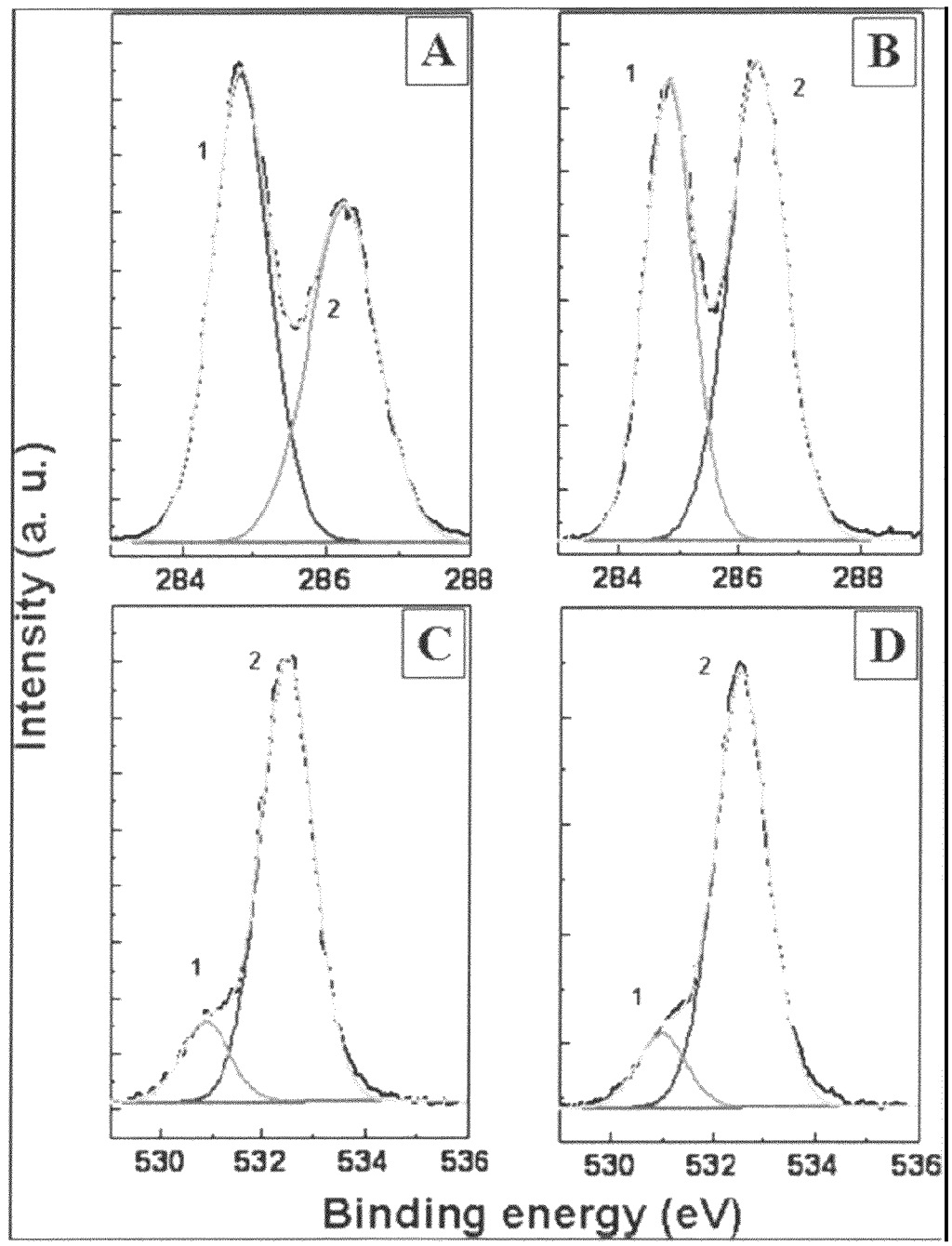
FIG. 8(a) to (d) are graphs showing C1s and O1s core level spectra recorded from a drop-cast film on a glass substrate from the CdS nanorods in aqueous phase that have been phase transferred with F127 (A) and (C) and with F88 (B) and (D), respectively. The chemically distinct deconvoluted components have been shown as curves 1 and 2 in parts (A) to (D)
Figure 10:
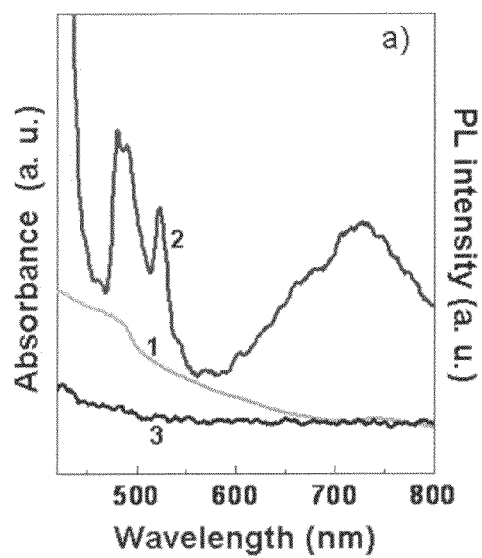
FIG. 10 (a) is a UV-Vis spectra of CdS nanorods phase transferred with F88 (curve 1) in the aqueous phase. Curves 2 and 3 are the emission spectra from the water dispersible CdS nanorods phase transferred by F88 and the pristine F88 copolymer respectively when an excitation wavelength of 350 nm was used, (b), (c) Representative TEM images of the aligned CdS nanorods in water at progressively higher magnifications after phase transfer with F88. The inset in (c) shows the selected area electron diffraction (SAED) pattern taken from the assembly of CdS nanorods.
Figure 10:
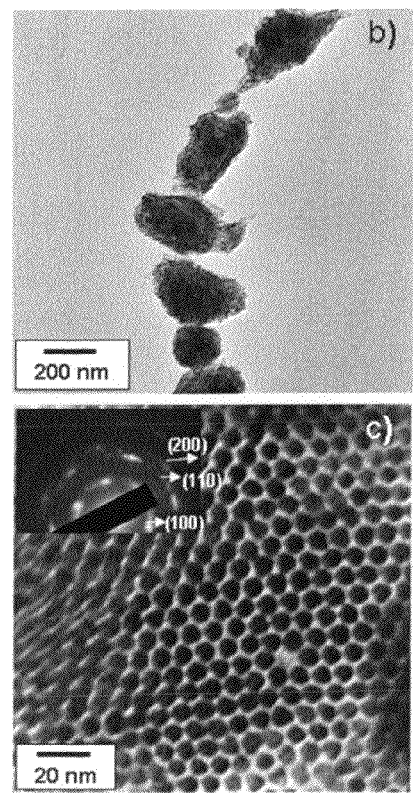
Figure 11:
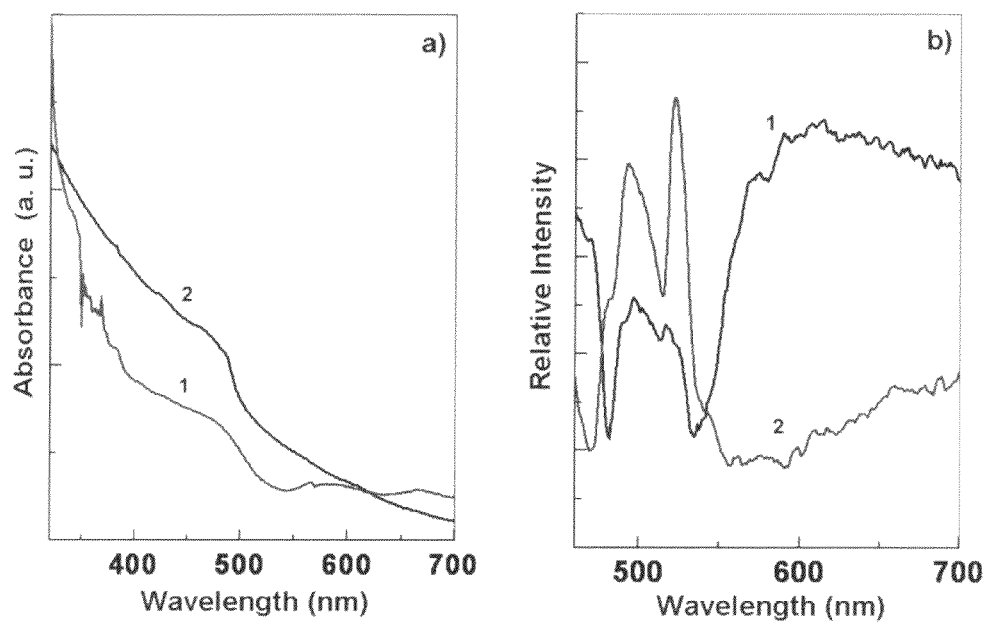
FIG. 11 is a UV-Vis (a) and PL emission spectra (b) of CdS nanorods as synthesized in the organic phase (curve 1) and after phase transfer with the block copolymer (curve 2) in the aqueous phase.
Figure 12:
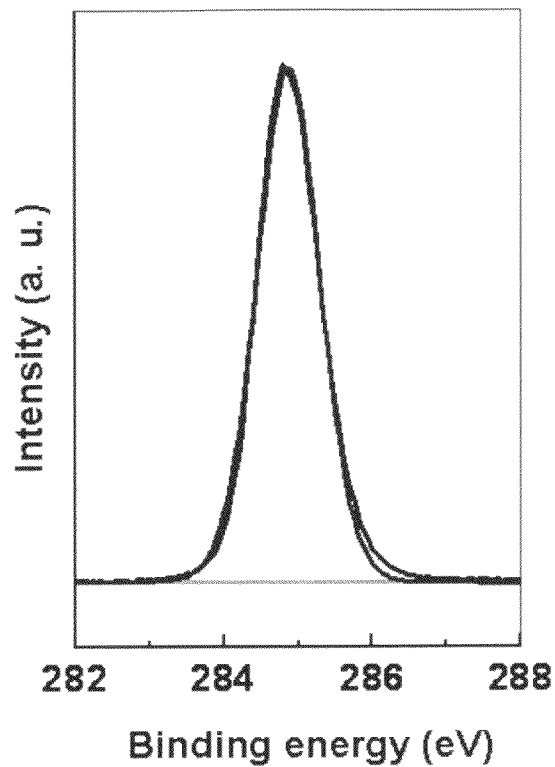
FIG. 12 is a C1s core level spectra of the as-prepared CdS nanorods dispersed in toluene.

The phase transfer of the nanorods was conducted by vigorous stirring of the nanorod—toluene solution with an aqueous solution containing triblock pluronic copolymers. During this process, the transfer of CdS nanorods from the organic to the aqueous phase could be followed visually (FIG. 3A) where the bright yellow color of the CdS nanorods in toluene was transferred to the aqueous layer containing 5 ml of 3% F127. The stirring speed of 50 rpm to 500 rpm also affected the size of the micelles formed with faster speeds resulting in smaller micelles. Aqueous solutions containing 3% and 5% F88 resulted in an incomplete transfer with the characteristic yellow color present in both the organic and the aqueous medium, FIG. 3B. A clear organic layer was only obtained when the concentration of F88 was raised to 20%, however, the aqueous layer became extremely viscous, due to excess surfactants, and could not be separated, FIG. 3B. P123 was also found to be quite effective at phase transfer, achieving 100% phase transfer with a 3% surfactant concentration, FIG. 3C. However, in this case, CdS nanorods from the aqueous phase were found to form a separate layer when further diluted with water. Probably, P123 was able to drag the rods into aqueous layer but not able to provide an effective hydrophilic environment for solubilising in a polar solvent thoroughly. P65 was found to be least effective, regardless of percentage weight in solution, and a vigorous stirring of organic and aqueous layer generated an emulsion inseparable (FIG. 3D) even after 3 days. Visual observation of the yellow color from the aqueous part of F127 solution was in accord with the UV-Vis and photoluminescence spectra (FIG. 3E, curves 1 and 3) which show characteristic features similar to CdS. synthesized in the organic medium. The emission peak for F127 phase transferred CdS nanorods (curve 3 in FIG. 3E) centred at about 490 nm (band gap=about 2.53 eV) is almost 30 nm blue-shifted as compared to the emission spectra of bulk CdS (ca. 510 nm). This is probably due to an enhanced quantum confinement within the nanorods. The presence of a satellite peak. (about 523 nm, green shifted) instead of a single sharp peak is possibly from the group of nanorods, a phenomenon which is generally observed when the nanorods are not isolated and are coupled to other nanocrystals [24]. The other broad absorption band ranging from 650-800 nm is generally attributed to the emission caused due to non-radiative decay of surface trap states of the semiconductor materials. In contrast, pristine F127 did not produce any emission in the visible region when excited at 350 nm (curve 2, FIG. 3E). FIG. 3F shows the transmission electron micrograph of F127 protected CdS nanorod super crystals (NRSCs), ranging from 100-600 nm, that have resulted after a phase transfer to the aqueous medium. A higher magnification image, FIG. 3G, shows that each consists of an ensemble of axially aligned and close packed CdS nanorods. The inter-rod distance of the CdS phase transferred nanorods (FIG. 9b) was found to be about 3.5 nm. Interestingly, this is comparable to the inter-particle distance obtained when the same nanorods are assembled on a substrate from an organic solution under highly oriented pyrolytic graphite (HOPG) as reported previously [12] (FIG. 9a). The absence of enhancement in the inter-rod spacing in the NRSCs when compared to rods assembled under HOPG strongly suggests that the rods are still tethered only by the long chain alkyl ligands in the close packed assembly. The triblock copolymer therefore does not interact individually with each alkyl capped rod but encloses a group or rods as an ensemble. The selected area electron diffraction (SAED) pattern obtained from F127 capped CdS nanorods, inset of FIG. 3G, is indexed to the reflections of wurtzite CdS (a, b=4.1409 Å, c=6.7198 Å°, PCPDF file no.: 41-1049). Similar results were obtained in the case of phase transfer of CdS nanorods by F88 where NRSCs ranging from 100-400 nm were obtained with the individual rods being perpendicularly aligned within these structures. The UVVis and PL spectra along with representative TEM images of the F88 transferred CdS nanorods are shown in FIG. 10. Although the UV-Vis spectra of as synthesized CdS nanorods in toluene were similar to that of the assembled nanorods in aqueous medium, there was a difference in the emission spectra from the assembled nanorods which may suggest a compound effect from the corralled nanorods in aqueous medium (FIG. 11). Phase transfer with CdSe nanorods and CdTe dipods/tetrapods which were previously prepared through a similar pyrolytic route[4] having ODPA/OPA/HPA/TOPO as the surface capping agent was also studied. The phase transfer of monodisperse CdSe nanorods resulted in the formation of individual NRSCs ranging from 20 300 nm, FIG. 4A. A further magnified image, FIG. 4B, shows that NRSCs of similar size can further organise on a larger scale into a pseudo-hexagonal arrangement that mimics the close packing of individual rods within each super crystal (inset, FIG. 4B). A high resolution image, FIG. 4C, of nanorods within an NRSC shows the lattice parameter (0.35 nm) from the highly oriented crystallographic planes (002) of the individual nanorods. The CdSe NRSCs were more monodisperse than equivalent CdS NRSCs and showed remarkably high water dispersibility requiring high centrifugation speeds for precipitation. Judicious size selection of the NRSCs was achieved by sequentially increasing the speed with the largest (>200 nm) precipitating at 5500 rpm (FIG. 4D) and the smallest (20-80 nm) at 13 000 rpm (FIG. 4E). The smallest NRSCs which form a discernible disc from the axial alignment and close packing of nanorods were typically 40-50 nm in diameter, FIG. 4F. TEM images (FIG. 4G-I) of phase transferred CdTe dipods/tetrapods are somewhat different, though assembly can be found in some regions of the sample (FIGS. 4G and H). The lack of NRSC formation tendency in tetrapods can be attributed to the fact that dipods/tetrapods cannot be compressed easily like nanorods in the form of compact close packed structures. In spite of this fact, CdTe tetrapod-assemblies are somewhat formed and transported to the aqueous phase which clearly establish the efficacy of F 127 for phase transfer of semiconductor nanocrystals. To prove the crystalline nature of phase transferred CdSe and CdTe, SAED patterns are given as inset in FIGS. 4C and I, respectively, which correspond to the wurtzite structures (CdSe: a, b=4.299 Å, c=7.010 Å, PCPDF file no.: 08-0459; CdTe: a, b=4.58 Å, c=7.5 Å, PCPDF file no.: 19-0193). X-Ray photoelectron spectroscopy (XPS) of the CdS nanorods phase transferred by F127 and F88 was also performed. The C1s spectra in FIGS. 8A and B clearly show the presence of 2 component peaks. The lower binding energy peak at 284.8 eV is assigned to carbon bonded to carbon or hydrogen. The appearance of a second component peak at 286.3 eV (deconvoluted curve 2 in FIGS. 8A and B) can be assigned to C—O bonding present in both F127 and F88. The O1s spectra, FIGS. 8C and D show the related oxygen from the C—O bond appearing at 532.5 eV. The ratio of C:O for the C—O bonding is 2.1 and 1.9 for F127 and F88 transferred CdS nanorods, respectively. This is in good agreement with the C:O ratio from the molecular formula of the ether linkages in F127 ($PEO_{106}PPO_{69}PEO_{106}$) and F88 ($PEO_{102}PPO_{39}PEO_{102}$). In contrast, C1s peak of only ODPA/TOPO capped CdS nanorods in the organic medium did not show any such high energy C1s peak corresponding to C—O (FIG. 12). The C—O containing species in the phase transferred samples constitute 50-60% of the surface composition as determined by XPS. In addition, the intensity of the alkyl peak (284.8 eV) corresponding to surfactant species decreases by half relative to that of CdS nanorods in the absence of the polymer, while the ratio of alkyl C:Cd of the nanorods remains comparable. This can be viewed as resulting from the screening effect imposed by the polymer, which supports the postulation that the polymer encapsulates the nanorods ensemble by interacting with the capping layer. The proposition of encapsulation of a group of nanorods by F127 was further supported by scanning electron microscope (SEM) images. Discrete NRSCs could be resolved by SEM and at low resolution the structures appear as a mixture of spherical and anisotropic particles, FIG. 5A. HRSEM, FIG. 5B (scale bar=100 nm) and further magnified image in FIG. 5C (scale bar=50 nm), revealed the individual nanorod close packing within the structures which forms a perfect hexagonal framework. The HRSEM image further confirms that all the NRSCs have a disc morphology predominantly consisting of a single monolayer of axially aligned rods. In the NRSC labeled 1 (FIG. 5B) the disc has come to rest flat on the substrate whereas in 2 the disc is on its edge. Some stray rods lie in a parallel orientation on the 2D assemblies but the predominant rod orientation is close packed within the disc. An estimate on a single NRSC as shown in the magnified image of FIG. 5C revealed that as many as about 800 nanorods are bound together in this hexagonal closed-packed assembly. The occurrence of 2D assembly from nanorods in solution suggests a significant driving force for side by side packing of the rods. This effect parallels that observed from nanorods assembled on a substrate where supercrystallisation was evident with the nanorods finding their preferred place on the growing assembly before locking in thus allowing the lowest energy consideration to be reached [11, 12, 15]. Clearly, the similar formation of highly ordered nanorod discs from randomly dispersed nanorods in solution suggests a similar phenomenon is occurring on phase transfer. Particle size analysis, optical microscopy (FIG. 13A) and the ability to selectively precipitate by mass (centrifuge) or by size (filtration, FIG. 13 B, C) confirmed that the NRSCs were real features present in solution and do not occur due to solvent evaporation.

Advantages

This method involves a very simple process of reverse phase transfer at room temperature of semiconductor nanorods from the organic to the aqueous phase where on transfer, the rods are corralled into assemblies which are completely dispersed.

This method offers the flexibility of using a range of other semiconductor materials that can be phase transferred to the aqueous medium which form the ideal materials for subsequent use in biological systems, for example semiconductor nanorod groups IV, II-VI, III-V, and metal nanorods such as Cu, Fe (all transition metals) and Ag and A.

Large scale synthesis possible as the process is not selective to the initial concentration of the semiconductor nanorods.

Effective size control of the nanorods super assemblies through centrifugation/filtration that matches with cell specific applications.

High stability of the assemblies in the aqueous medium.

Ambient experimental conditions.

Application of the assemblies through internalization in a cellular system showing significant fluorescence intensity signal which allowed visualizing of all minor structural details of cell shape, cell surface morphology and adhesion to substrate.

Strong fluorescence, cellular uptake and prolonged persistence in the human cells (up to 7 days in this study) make these ensembles potentially useful as fluorescent probes in: gene delivery approaches; flow cytometry techniques; cell-scaffold interaction studies; tissue engineering; biomedical imaging; disease diagnosis; detection infection agents and DNA markers.

Figure 3:
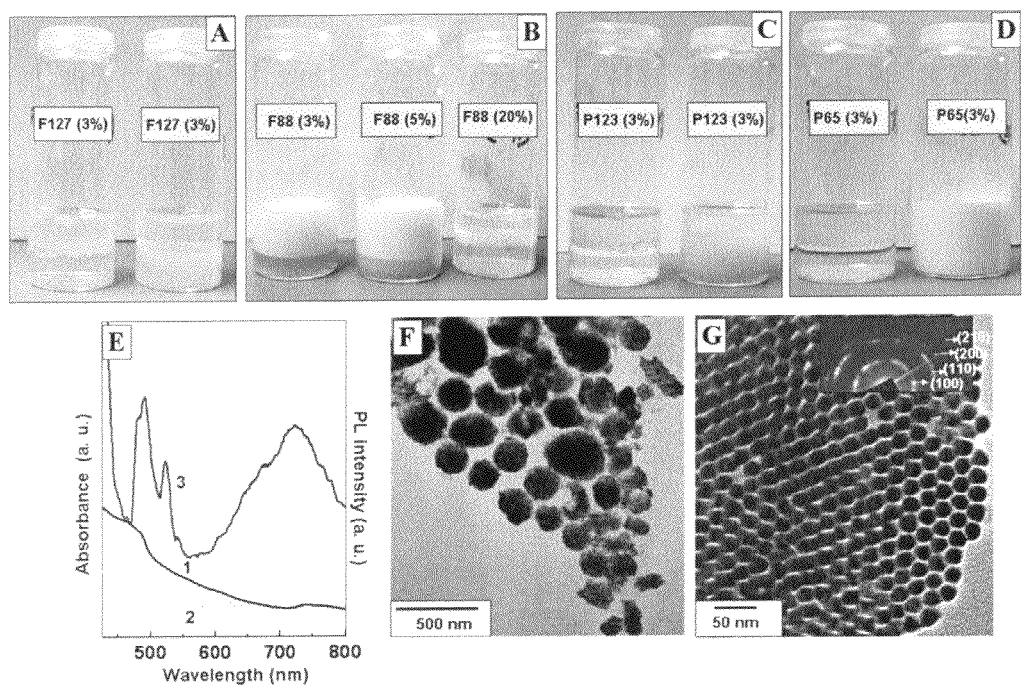
FIGS. 3(a) to (d) are images of sample vials for nano-rods.
FIG. 3(e) is a plot of photoluminescence spectra and FIGS. 3(f) and (g) are images showing alignment of nano-rods and selected area electron diffraction.
Figure 4:
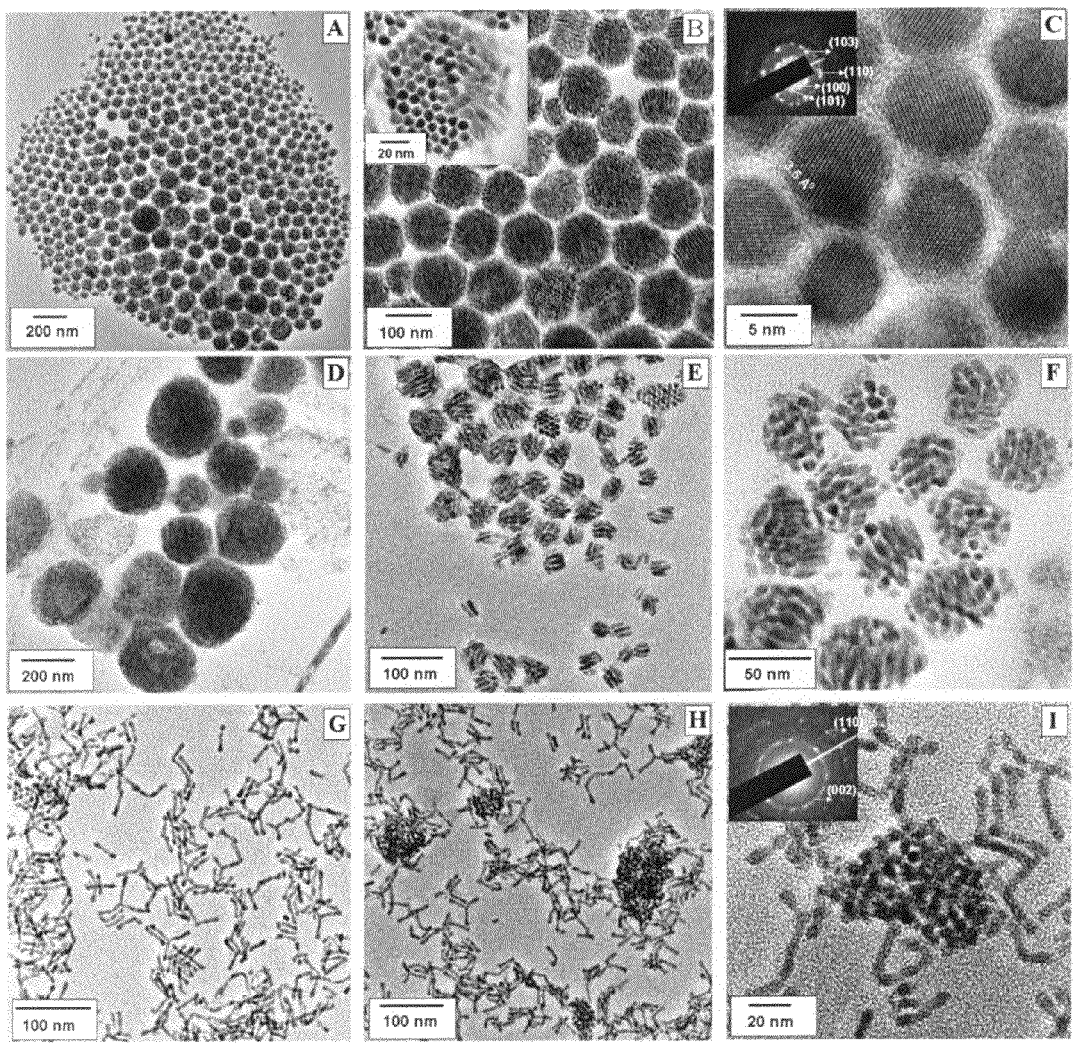
FIGS. 4(a) to (i) are images of materials at various stages of nano-rod processing.

FIG. 3 shows macroscopic, optical and electronic characterization of phase transferred CdS nanorods. (A) Photographs of sample vials showing the phase transfer of CdS nanorods from toluene with 3% F127, (B) 3%, 5% and 20% F88, (C) 3% P123 and (D) 3% P65 into water. In FIGS. (A), (C) and (D) CdS nanorods are in toluene in the bottle on the left-hand side (upper layer), whereas they are transferred to the aqueous phase (bottom layer) in the right-hand side bottle. (E) UV-Vis and photoluminescence spectra of CdS nanorods phase transferred with F127 (curves 1 and 3 respectively) in the aqueous phase. Curve 2 is the emission spectra of pristine F127. (F) Representative TEM images of the phase transferred CdS nanorods in water by F127 revealing NRSCs and (G) Perpendicular alignment of the nanorods magnified from one of the assemblies shown in F. The inset in (G) shows the selected area electron diffraction (SAED) pattern taken from the corresponding assembly of CdS nanorods.

Referring to FIG. 4 electron microscopy characterization of CdSe and CdTe samples (A) Representative TEM image of the formation of F127 mediated CdSe nanorod assemblies extending from 20-300 nm. Closed packed pseudo-hexagonal assembly of the nanorods is revealed in (B) and its corresponding inset shows the hexagonal stacking of the individual nanorods inside the micelle like structure. (C) High resolution TEM image of the individual nanorods within the NRSCs showing the crystallographic planes with the corresponding SAED pattern shown in the inset. Step-wise size selective centrifugation of NRSCs resulting in the larger (greater than about 200 nm, TEM image of D) and consequently smaller assemblies (about 20 to about 80 nm, TEM image of E). FIG. F shows the TEM image of the smallest disc (about 40 to about 50 nm) resulted from the alignment and packing of the individual nanorods. (G) Representative TEM image of the phase transferred CdTe dipods/tetrapods. (H) and (I) are TEM image snapshots of the CdTe solution showing formation of few assemblies as compared to that of CdSe. SAED pattern (inset of I) confirm the crystalline nature of the phase transferred CdTe NRSCs.

Figure 5:
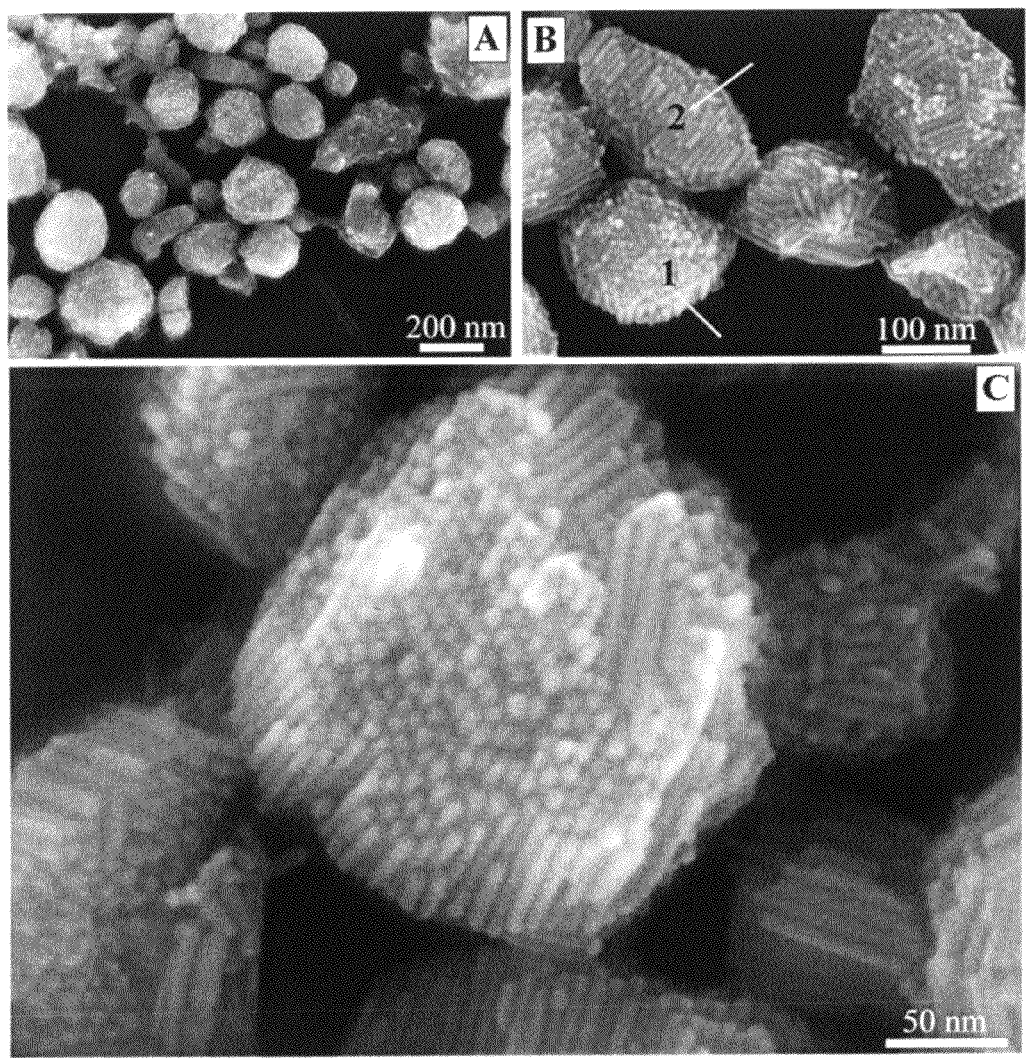
FIGS. 5(a) to (c) are images at different magnifications of CdS nano-rods.

Referring to FIG. 5 SEM, HRSEM of the NRSCs. (A) shows the SEM image CdS nanorods phase transferred by F127 in the aqueous phase showing different sized anisotropic nanorods assemblies. (B) HRSEM image where one of the NRSCs are lying flat (point 1) or are on its edge (point 2). (C) Further magnified image of one of the NRSCs revealing the multiple number of individual CdS nanorods stacked into a single structure.

Referring to FIG. 6 a reaction mechanism pathway is illustrated. Schematic showing the 3D orientation of the CdS nanorods in toluene and after reverse phase transfer to the aqueous phase with the help of copolymers via a micelle-type of structure.

FIG. 7 shows a preliminary investigation of the cellular biocompatibility of CdS assemblies, cellular uptake and maintenance of fluorescent properties of Cds assemblies after internalisation into the cytosol. (A) LSCM image of phase transferred CdS NRSCs. (Excitation laser $\lambda$=405 nm. Emission detection were collected in the range $\lambda$=420-480 nm), (B) Cellular uptake of CdS nanorods by VSM cells. LSCM images of CdS NRSCs adsorbed onto VSM cell outer membrane after 3 h incubation and internalisation of CdS NRSCs into the cell cytoplasm of VSMC cell via endocytosis can be observed on the cell surface membrane. After internalisation, spectral properties of the NRSCs are shifted to red spectra. Arrows shows the location of event of CdS uptake by the cells, (C) LSCM image of CdS NRSCs localised onto VSMC cell outer membrane after 24 h incubation and they are shown to produce only a fluorescence signal in the blue spectral region (Excitation laser $\lambda$=405 nm. Emission detection were collected in the range $\lambda$=420-480 nm), (D) Internalised CdS NRSCs into the cell cytoplasm of VSMC cell are shown to have an emission in the red spectral region $\lambda$=660-690 nm, (E) Total fluorescent signal from the CdS nanorods treated cell shown on a merged image of the two spectral detection channels.

Figure 9:
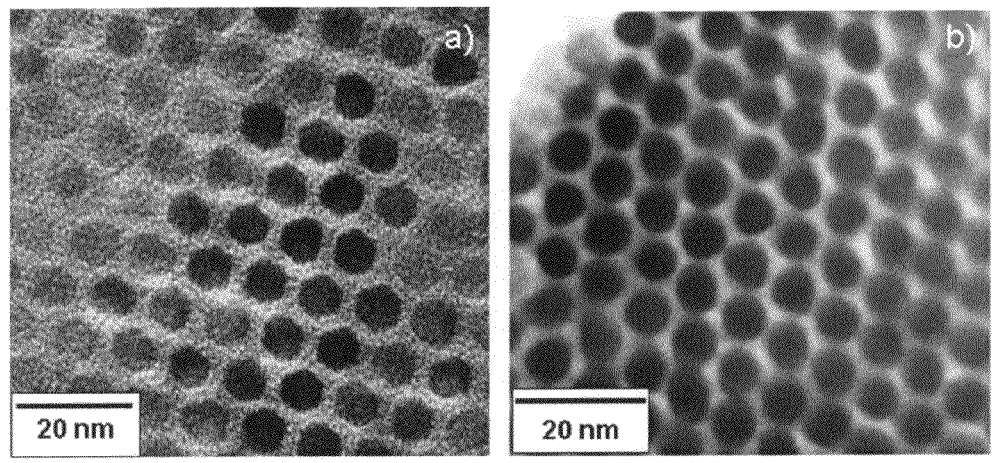
FIG. 9 (a) is a representative TEM images of the aligned CdS nanorods in toluene, (b) Similar alignment of CdS nanorods after phase transfer in water via F127 showing negligible change in the inter-rod distance.

The TEM images in FIG. 9 shows a comparison of the inter-rod distance between CdS nanorods assembly obtained by drop coating on a carbon-coated TEM grid form toluene (FIG. 9A) and that of after phase transfer to aqueous medium (FIG. 9B). A careful measurement revealed no significant difference in their inter-rod distance. This further supported the fact that the long chain polymer did not interact with individual nanorods but with a bunch of them, otherwise an increased rod to rod distance would have been observed in transmission electron microscopic image (FIG. 9B). The routine UV-Vis curve for CdS nanorods having an onset of absorption at 485 nm. This feature can be attributed to excitonic transitions in strongly quantized materials. Photo luminescence curve of the same CdS nanorods phase transferred by F88 excited at 350 nm was presented in curve 2. The photo luminescence emission of pristine F88 (curve 3) was also measured for comparison.

FIG. 10B illustrates the transmission electron micrographs of F88 protected CdS nanorods after phase transfer to the aqueous medium. FIG. 10B represent the presence of close-packed structure all over the grid in the low magnification similar to that observed when the phase transfer was initiated by F127 (FIG. 3F). FIG. 11 denotes a comparison of the UV-Vis and the PL spectra between the individual nanorods in toluene and the assembled rods after having phase transferred into the aqueous medium by the block copolymer. A comparison between the 2 states (non assembled individual nanorods in toluene versus the assembled ones in water) would involve a comparison of effects between two different media, however similar UV-Vis spectra (FIG. 11A, curves 1 and 2) but a conspicuous difference in the emission spectra was observed. There appears to be a considerable amount of decrease in the intensity of the broad emission band ranging from 580-700 when the rods are assembled in aqueous medium (curve 2 in FIG. 11B) in comparison to individual nanorods in toluene (curve 1 in FIG. 11B), a result which is consistent with the 2D assembly of CdS nanorods in organic medium reported by Chou et al.[14] This possibly entails significant amount of decrease of the non-radiative transition that occurs when the nanorods are dispersed in a chaotic fashion in toluene environment.

FIG. 12 represents C1s core level spectra with the chemically stripped components of as-synthesised CdS nanorods dispersed in toluene.

Figure 13:
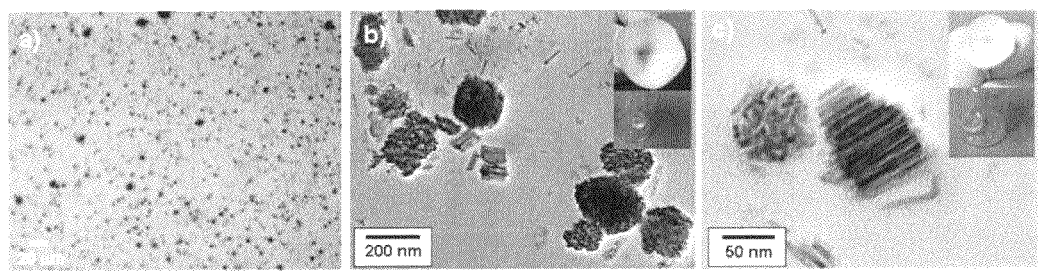
FIG. 13 (a) is a low magnification optical image of a droplet on a glass slide. Representative TEM image of the F127 mediated aqueous phase transferred CdS nanorods that have been filtered through Whatman filter grade 5 (b), pore size: 2.5 μm and when filtered through Milipore filter paper (c) pore size: 0.45 μm. The insets in (b) and (c) represent the photographs of the sample vials with the corresponding filter papers containing the filtrate and residue obtained during filtration of the CdS nanorods with 2.5 μm and 0.45 μm filter respectively.

FIG. 13 shows an optical micrograph of a droplet of phase transferred CdS nanorods on a glass slide indicating the presence of micron and submicron clusters in solution. The aqueous solution of phase transferred CdS nanorods was filtered through two different pore size filter papers, the first one being Whatman grade 5 (pore size ~2.5 micron) and the second one of Millipore (pore size ~0.45 micron). In the first case the entire solution passed through (pore size ~2.5 micron) and a TEM analysis of the filtrate (FIG. 12B) revealed no difference with FIG. 3F. The photograph of the empty filter paper along with bright yellow filtrate in the glass bottle is given as the inset of FIG. 12B. In the second experiment most of the CdS NRSCs were found to be trapped on the Millipore filter paper (~0.45 micron pore) and a very faint yellow colored filtrate was obtained (inset, FIG. 12C). Interestingly TEM showed no NRSCs but only individual rods dispersed on the grid. It can be inferred from this that the formation of CdS ensembles are real features in solution and do not arise due to deposition on substrates.

In another example, water dispersed clusters were also formed when the seed particles were zero dimensional nanocrystals instead of one dimensional rods.

Figure 14A:
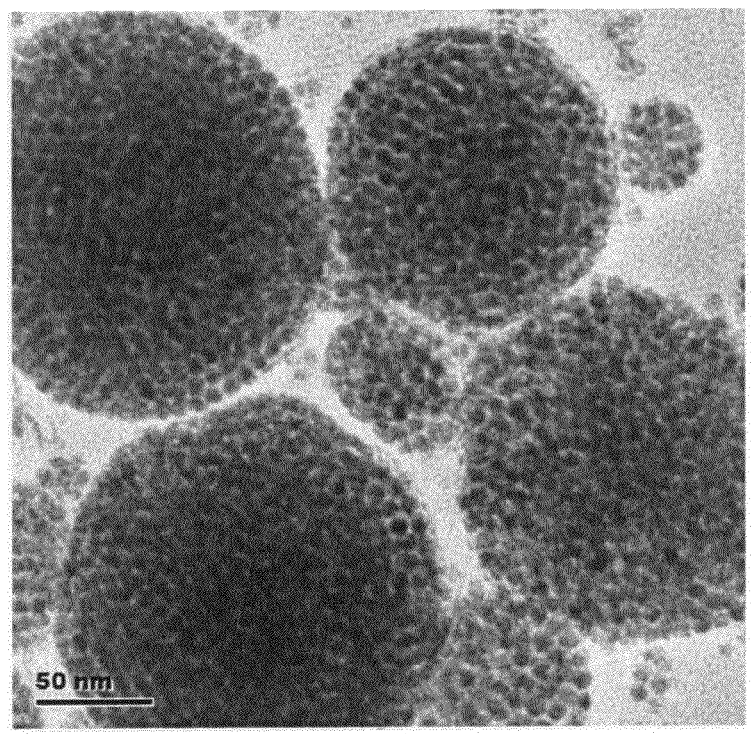
FIGS. 14(a) to (c) are images of assemblies of spherical nano-crystals produced according to the invention.
Figure 14B:
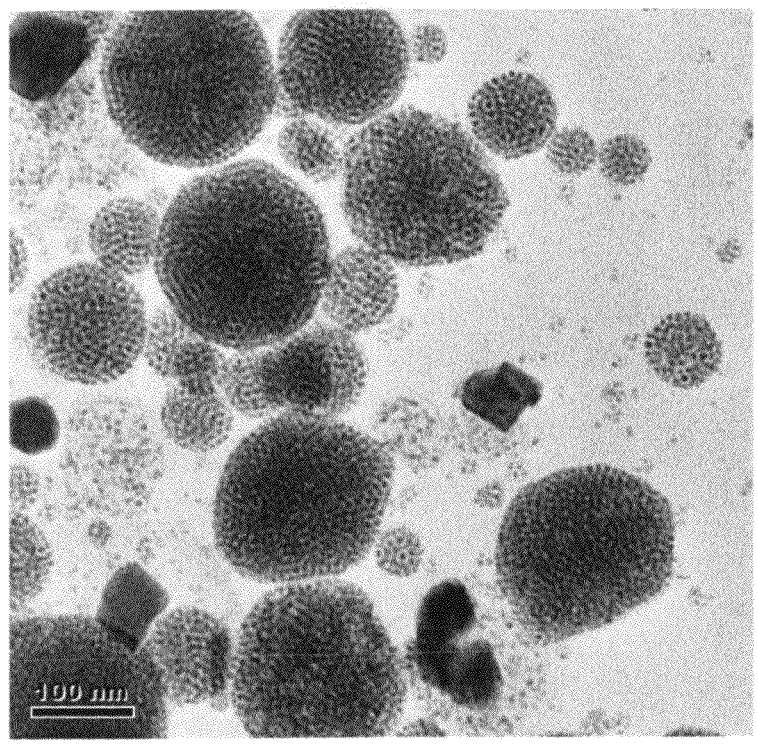
Figure 14C:
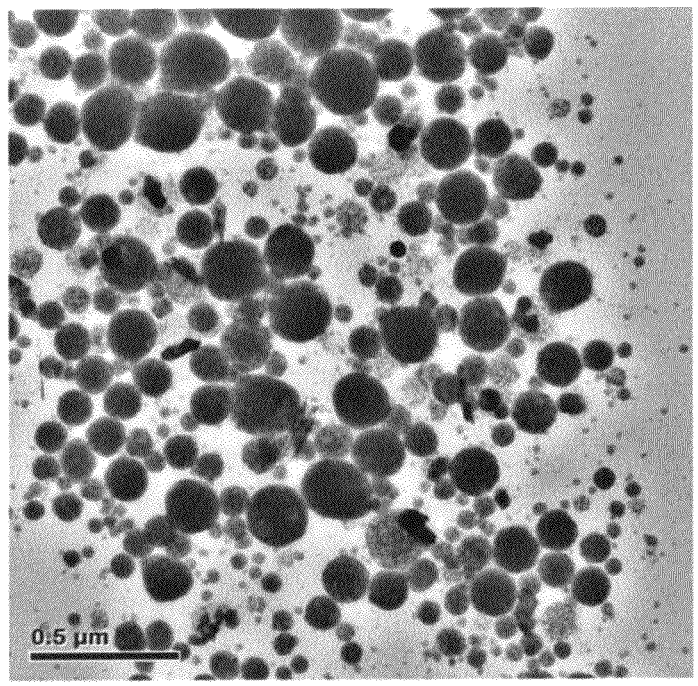

FIGS. 14 (a) to (c) show selected TEM images of spherical assemblies which have been phase transferred from the organic to the aqueous phase. The spherical assemblies are formed by the phase transfer of Ligand-capped 0D nanocrystals from the organic to the aqueous phase using tri-block copolymer surfactant using a similar approach to the 1D nanorods. The spherical nanocrystals that form the building blocks of these assemblies are either, CdS, CdTe, CdSe quantum dots, core shell quantum dots of ZnS—CdSe and ZnS—CdS and other combinations of semiconductorA-semiconductorB structures. The core-shell structures exhibit brighter photoemission.

In a typical synthesis, an organic solution of the alkyl capped nanoparticles is mixed with an aqueous solution of the triblock-copolymer. The concentration and composition (molar ratios of two or three different types of triblock) and temperature of reaction affect the sizes of the spheres formed. FIG. 14 (a-c) shows the largest spheres to be approximately 400 nm in size with the smallest of the order of 30 nm. Spheres of similar size can be formed by fine tuning the reaction parameters or separated by mass with a centrifuge.

The core-shell nanocrystal assemblies was also achieved with the nanorod structures.

It will be appreciated that the invention involves a simple process of reverse phase transfer at room temperature of semiconductor nanorods from an organic phase to an aqueous phase where upon phase transfer, the rods are corralled into assemblies which are completely dispersed.

This method offers the flexibility of using a range of other semiconductor materials that can be phase transferred to an aqueous medium which form very suitable materials for subsequent use in biological systems. For example semiconductor nanorods groups IV, II-VI, III-V or metal nanorods such as Cu, Fe (All transition metals) and Ag and Au could be used.

The process of reverse phase transfer is not selective to the initial concentration of the semiconductor nanorods which suggest the ease with which the process can be made scalable.

Nanorods phase transferred by this process can be efficiently internalized in a cellular system showing significant fluorescence intensity signal from the cluster treated cells (FIG. 7B to E) which allowed visualizing of all minor structural details of cell shape, cell surface morphology and adhesion to substrate.

Strong fluorescence, cellular uptake and prolonged persistence in the human cells (up to 7 days in this study) make these ensembles potentially useful as fluorescent probes in: gene delivery approaches; flow cytometry techniques; cell-scaffold interaction studies; tissue engineering; biomedical imaging; disease diagnosis; detection infection agents and DNA markers.

In general, the nanorod assemblies may comprise a functional group such as a biological and/or chemical group. The functional group may be selected from one or more of the group comprising: pharmaceutical compounds, drug molecules, therapeutic compounds, radioactive compounds, chemotherapy agents, nucleic acids, antibodies, proteins, peptides, MRI contrast agents, preservatives, flavor compounds, smell compounds, colored dye molecules, fluorescent dye molecules, enzyme molecules, pesticides, fungicides and fertilizers, another nanoparticles, bacteriophages, animal viruses, antimicrobial agents, activator of cell receptors, an adjuvant that enhances immune response to the antigen, materials that enhance the incorporation of genetic material or stimulate the immune response, immunosuppressant, natural polymers, hormones and steroids, chemotherapeutics, antibiotics, antifungal agents, anesthetics, immunomodulators, anti-inflammatory drugs, pain relieving drugs, autonomic drugs, cardiovascular-renal drugs, endocrine drugs, hematopoietic growth factors, blood lipid lowering drugs, antileptics, and psychoactive drugs, aptamers, oligonucleotides, chemotherapeutics (anti-cancer drugs), antibiotics, antifungal agents, anesthetics, immunomodulators (e.g., interferon, cyclosporine), anti-inflammatory and other types of pain relieving drugs, autonomic drugs, cardiovascular-renal drugs, endocrine drugs, hematopoietic growth factors, blood lipid lowering drugs, AIDS drugs, modulators of smooth muscle function, antileptics, psychoactive drugs, and drugs that act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species, cytokines, ribozymes, interferons, oligonucleotide sequences that inhibit translation or transcription of other genes, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth hormones such as human growth hormone and its derivatives such as methione-human growth hormone and des-phenylalanine human growth hormone, human and animal growth hormone, fertility inhibitors such as the prostaglandins, fertility promoters, growth factors such as insulin-like growth factor, coagulation factors and anticoagulation factors, Non-steroidal anti-inflammatory drugs (NSAIDs), and combinations thereof.

The invention is not limited to the embodiment hereinbefore described, with reference to the accompanying drawings, which may be varied in construction and detail.

The invention claimed is:

1. A method of processing nanoparticles comprising the steps of:
   (a) providing ligand-capped nanoparticles dispersed in an organic solvent; and
   (b) performing phase transfer of the nanoparticles by introducing into the organic solvent an aqueous solution of a polymer surfactant dissolved in water, and mixing the organic solvent and the aqueous solution until the polymer forms micelles which encapsulate the nanoparticles in assemblies.

2. The method as claimed in claim 1, wherein concentration of the polymer surfactant is controlled to tune the assembly size.

3. The method as claimed in claim 1, wherein temperature of the phase change reaction is controlled to tune the assembly size.

4. The method as claimed in claim 1, wherein rate of mixing is controlled to tune the assembly size.

5. The method as claimed in claim 1, wherein separation is performed after phase transfer to provide assemblies of a desired size range.

6. The method as claimed in claim 1, wherein separation is performed after phase transfer to provide assemblies of a desired size range, and said separation comprises centrifuging.

7. The method as claimed in claim 1, wherein the polymer surfactant is a copolymer.

8. The method as claimed in claim 1, wherein the polymer surfactant is a triblock copolymer.

9. The method as claimed in claim 1, wherein the polymer surfactant is a triblock copolymer which is lyophilic with a hydrophobic head group and two hydrophilic tails, and in the aqueous solution the hydrophobic components organize to form a micelle with a hydrophobic core in the centre and a hydrated shell in contact with water.

10. The method as claimed in claim 1, wherein the polymer surfactant is a triblock copolymer which is lyophilic with a hydrophobic head group and two hydrophilic tails, and in the aqueous solution the hydrophobic components organize to form a micelle with a hydrophobic core in the centre and a hydrated shell in contact with water, and wherein the hydrophobic tails are of approximately equal length.

11. The method as claimed in claim 1, wherein the nanoparticles are nanorods.

12. The method as claimed in claim 1, wherein the nanoparticles are nanorods covered with long-chain alkyl ligands which are hydrophobic and are compatible with a micelle core and are trapped there on phase transfer, in which a reduced volume of the core causes a close-packing of the nanorods into assemblies with sizes governed by the size of the micelle.

13. The method as claimed in claim 1, wherein the mixing comprises stirring with a stirring rate of about 50 rpm to about 500 rpm.

14. The method as claimed in claim 1, wherein the nanoparticles are formed from a semiconductor material.

15. The method as claimed in claim 1, wherein the nanoparticles are formed from one or more of CdS, CdSe and CdTe.

16. The method as claimed in claim 1, wherein the nanoparticles are formed from a metal.

17. The method as claimed in claim 1, wherein the nanoparticles are formed from one or more of Cu, Fe, Ag and Au.

18. The method as claimed in claim 17, wherein the nanoparticle assemblies have a size of between about 20 nm to about 500 nm.

19. The method as claimed in claim 1, wherein the organic solvent is toluene.

20. The method as claimed in claim 1, wherein the polymer is a copolymer selected from the group consisting of one or more of pluronic F127, F88, P123 and P65.

21. The method as claimed in claim 1, wherein the polymer is a copolymer present at a concentration of between about 1% to about 20% w/v based on the aqueous solution.

22. The method as claimed in claim 1, wherein the copolymer is present at a concentration of about 2% to 4% w/v based on the aqueous solution.

23. The method as claimed in claim 1, wherein the nanoparticle assemblies are separated after phase transfer by filtration.

24. The method as claimed in claim 1, wherein the nanoparticle assemblies are separated after phase transfer by filtration, and wherein the nanoparticles are filtered through a filter with a pore size of about 0.4 µm to 3.0 µm.

* * * * *